United States Patent
Butler et al.

(10) Patent No.: US 12,227,789 B2
(45) Date of Patent: Feb. 18, 2025

(54) METHODS, COMPOSITIONS, AND DEVICES FOR ISOLATION AND EXPRESSION ANALYSIS OF REGIONS OF INTEREST FROM A TISSUE

(71) Applicant: Quantumcyte, Inc., Sunnyvale, CA (US)

(72) Inventors: John Butler, San Jose, CA (US); Bidhan Chaudhuri, San Jose, CA (US)

(73) Assignee: QUANTUMCYTE, INC., Sunnyvale, CA (US)

(*) Notice: Subject to any disclaimer, the term of this patent is extended or adjusted under 35 U.S.C. 154(b) by 911 days.

(21) Appl. No.: 17/010,390

(22) Filed: Sep. 2, 2020

(65) Prior Publication Data
US 2021/0222229 A1    Jul. 22, 2021

Related U.S. Application Data

(63) Continuation of application No. PCT/US2019/020610, filed on Mar. 4, 2019.

(60) Provisional application No. 62/691,559, filed on Jun. 28, 2018, provisional application No. 62/637,998, filed on Mar. 2, 2018.

(51) Int. Cl.
*C12Q 1/6806* (2018.01)
*C12Q 1/6869* (2018.01)
*G01N 1/06* (2006.01)

(52) U.S. Cl.
CPC ........ *C12Q 1/6806* (2013.01); *C12Q 1/6869* (2013.01); *G01N 1/06* (2013.01)

(58) Field of Classification Search
CPC ...... C12Q 1/6806; C12Q 1/6869; G01N 1/06; G01N 33/6848
See application file for complete search history.

(56) References Cited

U.S. PATENT DOCUMENTS

| | | |
|---|---|---|
| 5,474,796 A | 12/1995 | Brennan |
| 11,311,476 B2 | 4/2022 | Litvack et al. |
| 2003/0148401 A1* | 8/2003 | Agrawal ............... B01L 3/5088 435/7.9 |
| 2004/0018611 A1* | 1/2004 | Ward ................ B01L 3/502761 435/287.2 |
| 2005/0130179 A1* | 6/2005 | Lyamichev .............. C12N 9/22 536/25.32 |

(Continued)

FOREIGN PATENT DOCUMENTS

| | | |
|---|---|---|
| JP | H09-500568 | 1/1997 |
| JP | 2010-510777 | 4/2010 |

(Continued)

OTHER PUBLICATIONS

Thompson ("Tandem Mass Tags: A Novel Quantification Strategy for Comparative Analysis of Complex Protein Mixtures by MS/MS"). Analytical Chemistry 2003 75 (8), 1895-1904 DOI: 10.1021/ac0262560 (Year: 2003).*

(Continued)

*Primary Examiner* — Jennifer Wecker
*Assistant Examiner* — Jonathan Bortoli
(74) *Attorney, Agent, or Firm* — Sheridan Ross PC

(57) ABSTRACT

Provided herein are structures and methods for isolating cellular components from at least one region of interest in a (Continued)

planar tissue section. Structures and methods as described can allow for isolation and tagging of tissue regions.

28 Claims, 16 Drawing Sheets

Specification includes a Sequence Listing.

(56) References Cited

U.S. PATENT DOCUMENTS

| | | | |
|---|---|---|---|
| 2007/0008390 A1* | 1/2007 | Cruchon-Dupeyrat | ............... G03F 7/0002 347/85 |
| 2008/0038740 A1* | 2/2008 | Reed | ............... C12Q 1/6851 435/6.16 |
| 2009/0142853 A1* | 6/2009 | Warrington | ....... B01L 3/502784 422/82.07 |
| 2009/0281250 A1* | 11/2009 | DeSimone | ........... C08G 65/007 427/508 |
| 2009/0289213 A1 | 11/2009 | Pipper et al. | |
| 2010/0256015 A1* | 10/2010 | Lim | ............... B01J 19/0046 506/13 |
| 2011/0177518 A1 | 7/2011 | Kartalov et al. | |
| 2014/0234873 A1 | 8/2014 | Leck et al. | |
| 2015/0322395 A1 | 11/2015 | Kartalov et al. | |
| 2016/0237397 A1* | 8/2016 | Guia | ............... C12M 33/14 |
| 2017/0252744 A1* | 9/2017 | Baroud | ............. B01L 3/502746 |

FOREIGN PATENT DOCUMENTS

| | | |
|---|---|---|
| WO | WO-2007094739 A1 | 8/2007 |
| WO | WO-2012029993 A1 | 3/2012 |
| WO | WO-2014184005 A1 | 11/2014 |
| WO | WO-2016166128 A1 | 10/2016 |
| WO | WO-2017021785 A1 | 2/2017 |
| WO | WO-2019169407 A1 | 9/2019 |

OTHER PUBLICATIONS

Pitt JJ. Principles and applications of liquid chromatography-mass spectrometry in clinical biochemistry. Clin Biochem Rev. Feb. 2009;30(1):19-34. PMID: 19224008; PMCID: PMC2643089. (Year: 2009).*

PCT/US19/20610 International Search Report dated Jul. 8, 2019.

EP19760668 extended European Search Report dated Feb. 11, 2022.

Singapore Patent Application No. 11202008266S Search Report and Written Opinion dated Apr. 11, 2022.

* cited by examiner

Slide on the left: stained microtomed liver tissue
Slide on the right: patterned microtomed liver tissue, stained post patterning 125um and 500um features on Liver 1mm and 250um features on Liver Custom Patterns Patterned Slide: Liver Tissue

PATTERNED SLIDE: 2MM FEATURES ON LIVER
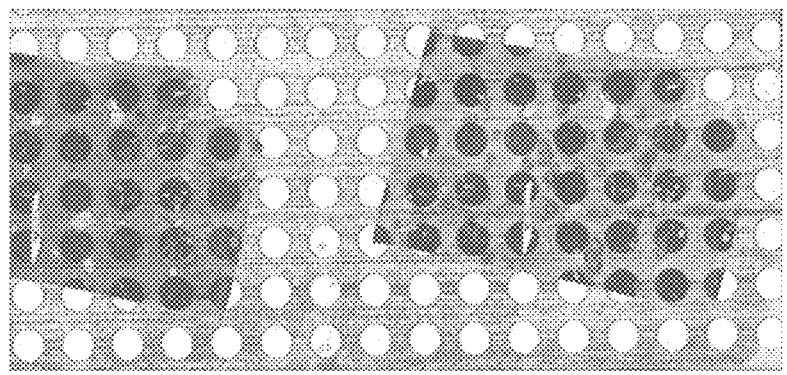
Patterned Slide: 2mm features on Liver Hydrophobic Masking Process Allows Isolation and Tagging of Tissue Regions without Specialized Equipment (Microfluidics, Lasers)

Freeform Delineation of Hydrophobic Mask Also Allows for Isolation of Particular Regions of Interest

- Custom ROIs may be defined e.g by microscopy combined with inkjet printing

FIGURE 6

Application of Spatially-Aware Barcodes Allow Deconvolution
of Gene Expression by Cell Type in Tissue

| Cell Type | Gene Expression Data | Sequence Data | Location |
|---|---|---|---|
| Myeloid | 1.Fasta | 1.Seq | A1 |
| Malignant | 2.Fasta | 2.Seq | C22 |
| Fibroblast | 3.Fasta | 3.Seq | G5 |
| T lymphocyte | 4.Fasta | 4.Seq | H8 |
| Dendritic | 5.Fasta | 5.Seq | N4 |
| B and T Lymphocyte | 6.Fasta | 6.Seq | T9 |
| T Lymphocyte | n.Fasta | n.Seq | F5 |

FIGURE 7
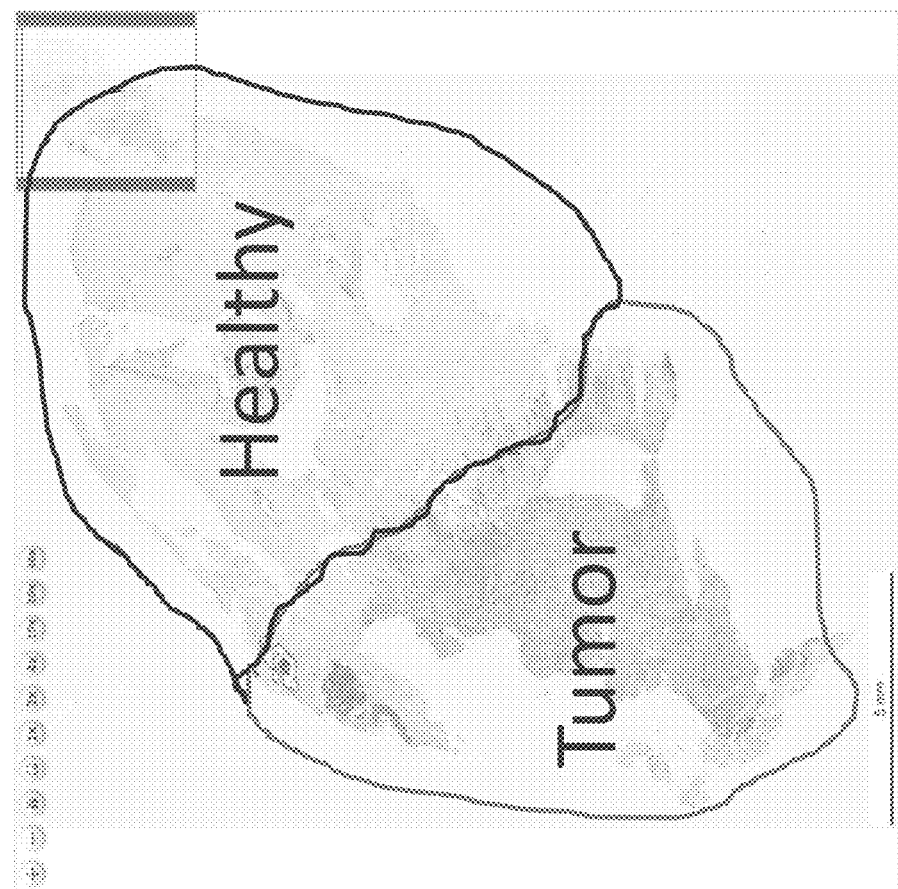
IHC Stain HER2+
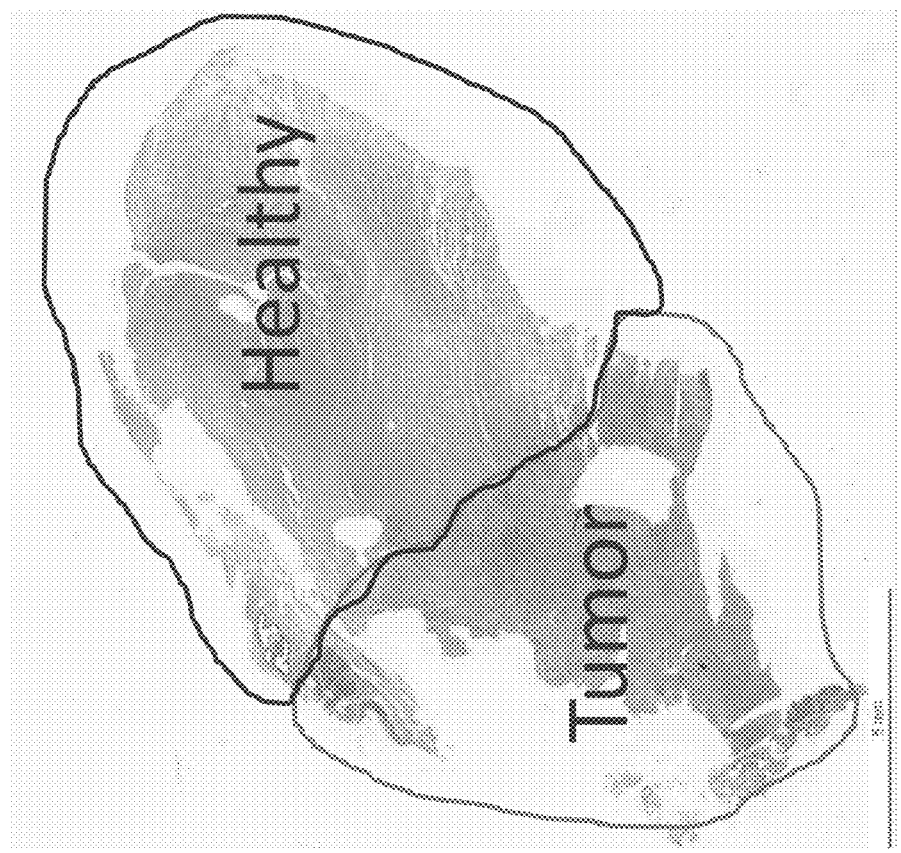
H and E Stain

FIGURE 8
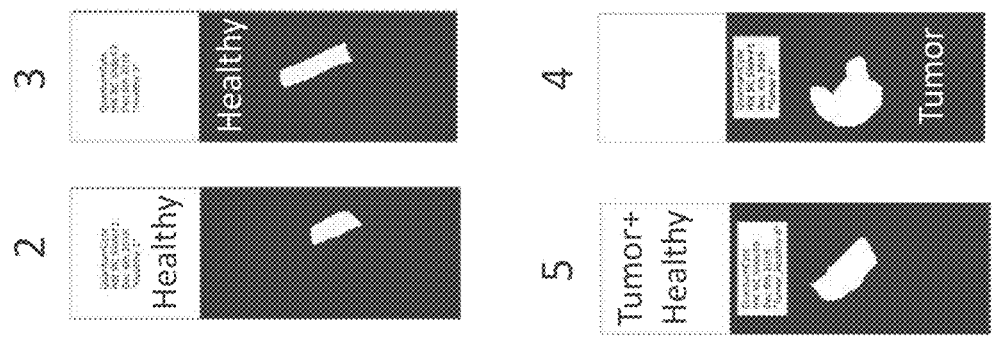
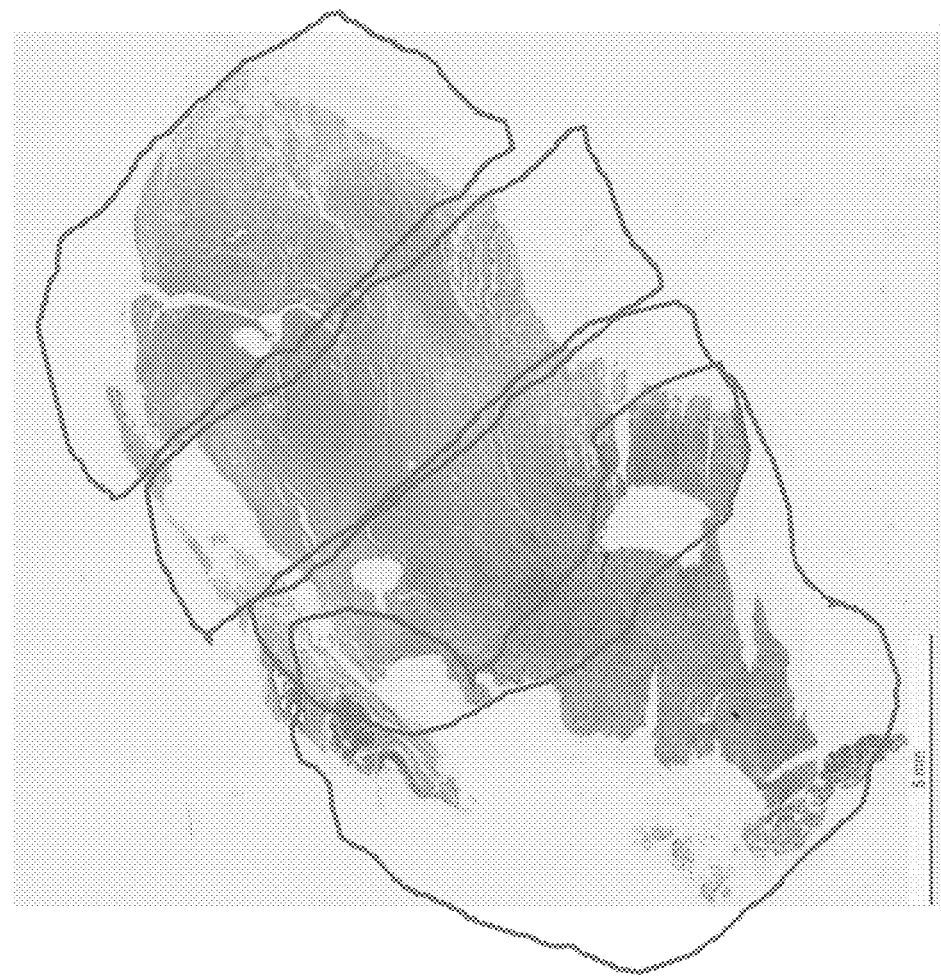

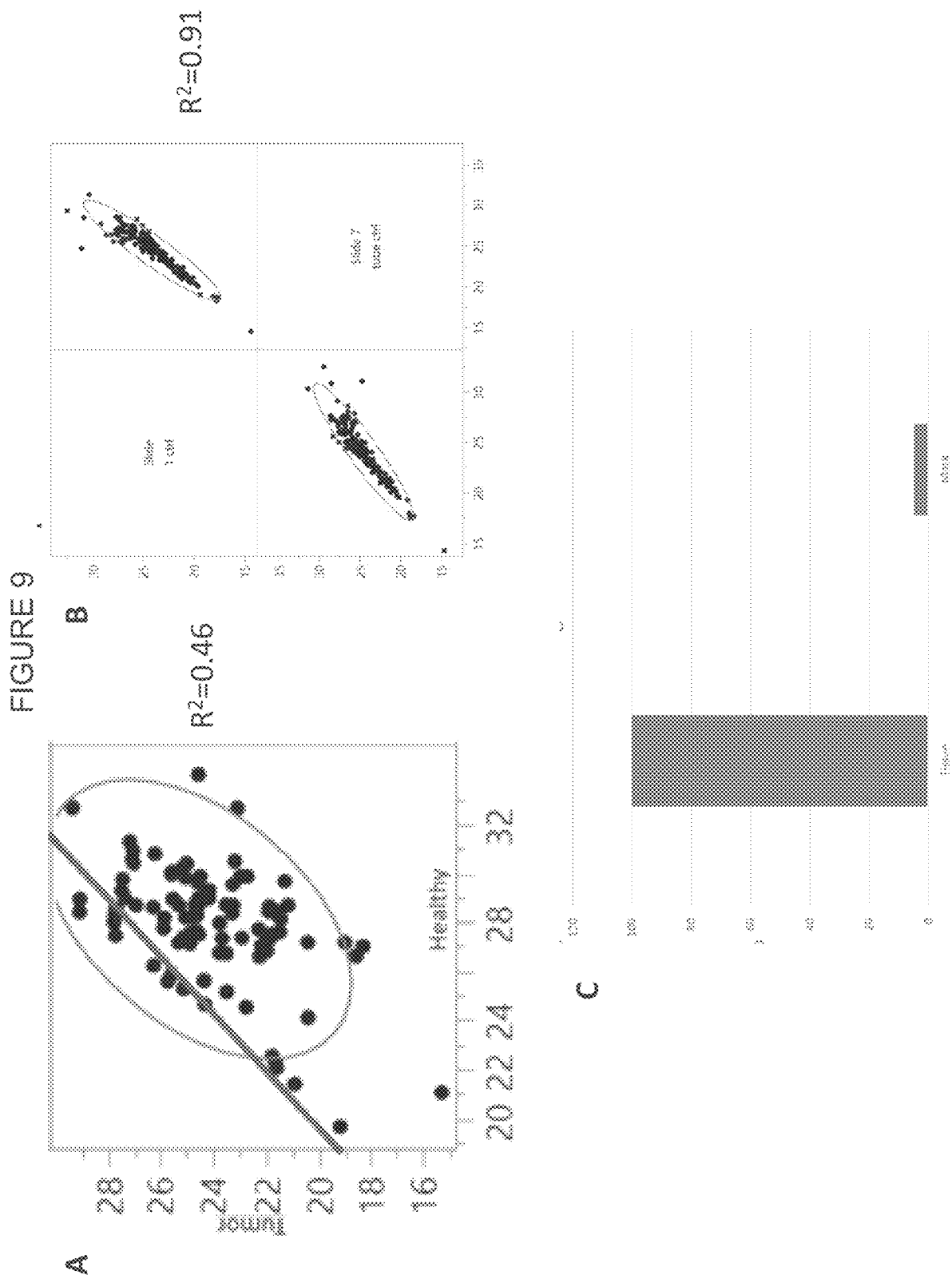

FIGURE 10B

Lysis buffer (the ⬤ drops) is delivered to each region using the same surface tension array that we have described previously. We think that the fluorosilane that covers the regions is physisorbed through hydrogen bonding or Van der Waals forces. This is based on a difference in water contact angle before and after lysis where the water contact angle is higher on the tissue before lysis. Also, we have demonstrated that we can extract RNA specifically from the regions using the KiSS transfer.

When we separate the slides the crude lysate follows the drops on the surface tension array.

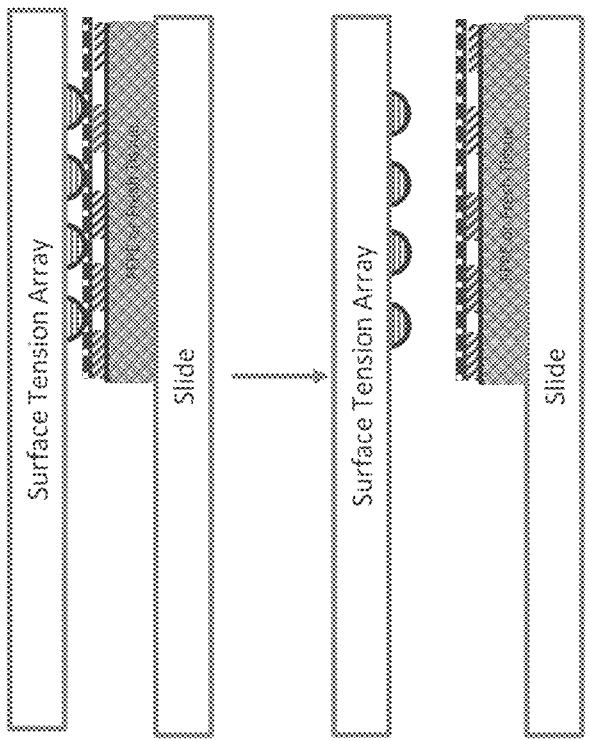

SEQUENCE LISTING

```
<160> NUMBER OF SEQ ID NOS: 13

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (29)..(30)
<223> OTHER INFORMATION: a, c, t, or g

<400> SEQUENCE: 1
cctttctctc ccttctctyy yyyyyyyynn                                    30

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (29)..(30)
<223> OTHER INFORMATION: a, c, t, or g

<400> SEQUENCE: 2
agagaaggga gagaaaggrr rrrrrrrrnn                                    30

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (29)..(30)
```

<223> OTHER INFORMATION: a, c, t, or g

<400> SEQUENCE: 3
ccaaacacac ccaacacamm mmmmmmmmnn                                30

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (29)..(30)
<223> OTHER INFORMATION: a, c, t, or g

<400> SEQUENCE: 4
tgtgttgggt gtgtttggkk kkkkkkkknn                                30

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cctttctctc ccttctctyy yyyyyyyy                                  28

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
agagaaggga gagaaaggrr rrrrrrrr                                  28

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ccaaacacac ccaacacamm mmmmmmmm                                  28

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tgtgttgggt gtgtttggkk kkkkkkkk                                  28

<210> SEQ ID NO 9
<211> LENGTH: 18
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 9
cctttctctc ccttctct                                                       18

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
agagaaggga gagaaagg                                                       18

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ccaaacacac ccaacaca                                                       18

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tgtgttgggt gtgtttgg                                                       18

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gtgagtgatg gttgaggtag tgtggag                                             27
```

METHODS, COMPOSITIONS, AND DEVICES FOR ISOLATION AND EXPRESSION ANALYSIS OF REGIONS OF INTEREST FROM A TISSUE

CROSS-REFERENCE TO RELATED APPLICATIONS

This application is a continuation of PCT Application No. PCT/US19/20610, filed Mar. 4, 2019, which claims priority to U.S. Provisional Application No. 62/691,559, filed on Jun. 28, 2018; and to U.S. Provisional Application No. 62/637,998, filed Mar. 2, 2018; the entireties of which are herein incorporated by reference.

SEQUENCE LISTING

The instant application contains a Sequence Listing which has been submitted electronically in ASCII format and is hereby incorporated by reference in its entirety. Said ASCII copy, created on Aug. 31, 2020, is named 44424-704_301_SL and is 3,639 bytes in size.

BACKGROUND OF THE INVENTION

Conventional clinical analysis of gene and protein expression from tissue samples involves extraction of nucleic acids and proteins from sections (e.g. biopsies of tissue). Absent a selection mechanism, analyses based on these sections represent a composite of expression profiles and DNA/RNA sequence data of a variety of cell types (e.g. epithelial, connective, and immune) within a tissue.

SUMMARY OF THE INVENTION

In some aspects, the present disclosure provides for a method of isolating biomolecules from at least one region of interest on a planar tissue section on a solid substrate for sequencing or analysis, comprising: (a) circumscribing defined regions of interest on the planar tissue section on a solid substrate with a polymer to form a nonphysical fluid barrier, wherein the region of interest is smaller than 1 mm in diameter; and (b) selectively disrupting in situ cells within the at least one defined region of interest. In some aspects, the present disclosure provides for a method of isolating biomolecules from at least one region of interest on a planar tissue section on a solid substrate for sequencing or analysis, comprising: applying to the planar tissue section a chemical mask circumscribing the at least one region of interest in the planar tissue section on a solid substrate, wherein the chemical mask forms a barrier suitable for selective disruption of cells within the at least one region of interest, wherein the chemical mask is not a physical fluid barrier. In some aspects, the present disclosure provides for a method of isolating biomolecules from at least one region of interest on a planar tissue section on a solid substrate for sequencing or analysis, comprising: dispensing a solvent suitable for disruption of cells within the region of interest in the planar tissue section on a solid substrate to form a droplet containing liberated cellular components, wherein the droplet is isolated from fluid communication from tissue outside the region of interest without a physical barrier. In some aspects, the present disclosure provides for a method of isolating and detecting biomolecules from a plurality of regions of interest in a tissue section, comprising: applying a hydrophobic mask to a tissue section such that at least 1000 regions of interest in the planar tissue section are isolated from fluid communication with each other without a physical barrier and detecting a plurality of proteins or nucleic acids liberated in situ from cells within the at least 1000 regions of interest, such that the spatial location information of the proteins or nucleic acids is retained. In some embodiments, the method is capable of isolating regions of interest smaller than or equal to about 100 microns in diameter. In some embodiments, the tissue section is an FFPE tissue section. In some embodiments, the method comprises detecting a plurality of proteins or nucleic acids liberated in situ from the cells, and the detecting comprises sequencing the nucleic acids liberated in situ from the cells. In some embodiments, the sequencing comprises tagging the nucleic acids liberated in situ with barcodes that identify the locations of the regions of interest. In some embodiments, the barcodes are not linked to a surface. In some embodiments, the tagging comprises tagging RNA liberated in situ and involves (a) applying oligonucleotides containing unique nucleic acid sequences to the at least 1000 regions of interest; and (b) performing $1^{st}$ and $2^{nd}$-strand cDNA synthesis on the at least 1000 regions of interest such that the regions of interest are isolated from each other. In some embodiments of this method, there is reduced cross-contamination of the unique nucleic acid sequences between cDNA molecules synthesized from the regions of interest. In some embodiments, the $1^{st}$-strand cDNA synthesis is performed in situ. In some embodiments, the $1^{st}$ and $2^{nd}$-strand cDNA synthesis is performed in situ. In some embodiments, the sequencing the nucleic acids liberated in situ from the cells comprises sequencing both mRNA and genomic DNA. In some embodiments, the sequencing the nucleic acids liberated in situ from the cells comprises sequencing mRNA. In some embodiments, the sequencing mRNA comprises a pre-amplification step performed on cDNA generated from the mRNA.

In some embodiments, the pre-amplification step is LM-PCR, PCR with random hexamer primers, PCR with poly-A specific primers, or any combination thereof. In some embodiments, the sequencing the nucleic acids liberated in situ from the cells comprises sequencing genomic DNA. In some embodiments, the sequencing genomic DNA comprises a whole genome amplification (WGA) step performed on the genomic DNA. In some embodiments, the WGA step is degenerate-oligonucleotide-primed (DOP) PCR, multiple-displacement-amplification (MDA), Multiple Annealing and Looping-Based Amplification Cycles (MALBAC), PicoPlex, isothermal amplification with self-degenerate primers, or a combination thereof.

In some aspects, the present disclosure provides for a tissue section, comprising thereupon at least 1000 aqueous droplets that are isolated from fluid communication with each other without a physical barrier. In some embodiments, the tissue section comprises a hydrophobic mask isolating the 1000 aqueous droplets from fluid communication with each other. In some embodiments, the at least 1000 aqueous droplets comprise at least 1000 unique oligonucleotides. In some embodiments, the hydrophobic mask comprises at least a layer of cyanoacrylate polymer. In some embodiments, the hydrophobic mask comprises at least a non-silylated fluoroalkyl layer. In some embodiments, the non-silylated fluoroalkyl layer comprises a fluoroacrylate or non-silylated perfluoroalkane compound. In some embodiments, the tissue section comprises at least a perfluoroalkyl silane layer. In some embodiments, the perfluoroalkyl silane layer comprises a perfluoroalkyltrichlorosilane or a perfluorotris(dimethylamino)silane. In some embodiments, the perfluoroalkyltrichlorosilane is FOTS (tridecafluoro-1,1,2,2- tetrahydrooctyl) trichlorosilane). In some embodiments, the perfluoroalkyltris(dimethylamino)silane is PF10TAS (perfluorodecyltris(dimethylamino)silane). In some embodiments, the oligonucleotides are not linked to a surface.

In some aspects, the present disclosure provides for a method of isolating cellular components from at least one region of interest in a planar tissue section on a solid substrate, comprising: (a) applying to the planar tissue section a chemical mask circumscribing the at least one region of interest in the planar tissue section on a solid substrate; and (b) solubilizing cellular components within the at least one region of interest by dispensing a solution comprising one or more extraction agents onto the region of interest, thereby selectively lysing cells circumscribed within the at least one region of interest. In some embodiments, the dispensing the solution onto the region of interest comprises: (a) dispensing the solution comprising one or more extraction agents onto an agent transfer device comprising at least one agent transfer array element positioned on a surface of a second solid substrate; (b) contacting the at least one agent transfer array element positioned on the surface of the second solid substrate to the planar tissue section, such that the at least one agent transfer array element spatially corresponds to the at least one region of interest in the planar tissue section, wherein the contacting allows the solution comprising the one or more extraction agents to be transferred to the at least one region of interest in the planar tissue section, thereby solubilizing the cellular components in the at least one region of interest in the solution comprising the one or more extraction agents. In some embodiments, the method further comprises isolating at least one solubilized cellular component from the at least one region of interest in the planar tissue section on the solid substrate. In some embodiments, the method comprises sequencing nucleic acids among the cellular components solubilized from the at least one region of interest. In some embodiments, the method comprises performing tandem mass spectrometry on proteins among the cellular components solubilized from the at least one region of interest. In some embodiments, the solution in (b) further comprises a soluble tag, wherein the soluble tag corresponds to the at least one region of interest. In some embodiments, the soluble tag is an oligonucleotide. In some embodiments, the oligonucleotide comprises a sample index sequence corresponding to the region of interest and, optionally, a unique molecular identifier sequence. In some embodiments, the oligonucleotide comprises a charge tag corresponding to the region of interest. In some embodiments, the oligonucleotide is double-stranded. In some embodiments, the oligonucleotide is conjugated to a bead. In some embodiments, the soluble tag is a Tandem Mass Tag. In some embodiments, the one or more extraction agents comprise one or more surfactants, proteases, tonicity adjusting agents, chaotropes, nucleases, buffers, protease inhibitors, phosphatase inhibitors, or nuclease inhibitors. In some embodiments, the chemical mask has a contact angle of 60-155 degrees. In some embodiments, the chemical mask is applied via a hydrophobic mask solution comprising a fluoroalkane or a fluoroacrylic polymer. In some embodiments, the chemical mask solution is applied via a solution comprising an acrylate or cyano-acrylate. In some embodiments, the chemical mask solution further comprises a solvent. In some embodiments, the solvent is a propylene glycol derivative, a fluorocarbon, or an alcohol. In some embodiments, the solvent is perfluorooctane, perfluoro-2-methylpentane, perfluoro-1,3-dimethylcyclohexane, perfluorodecalin, or 1,3-difluoropropane. In some embodiments, the at least one region of interest is circular, and the diameter of the region of interest is 1 mm or less, 500 microns or less, 250 microns or less, 125 microns or less, 100 microns or less, 80 microns or less, 50 microns or less, 25 microns or less, or 15 microns or less. In some embodiments, the at least one region of interest is less than about $7.8 \times 10^5$ square microns in area. In some embodiments, the at least one agent transfer array element positioned on the surface of the second solid substrate comprises at least one hydrophilic region circumscribed by a hydrophobic region. In some embodiments, the at least one agent transfer array element positioned on the surface of the second solid substrate is capable of delivering a volume of solution 10,000 picoliters or less, 1,000 picoliters or less, 500 picoliters or less, 250 picoliters or less, 100 picoliters or less, 50 picoliters or less, 10 picoliters or less, or 2 picoliters or less. In some embodiments, the hydrophobic region circumscribing the at least one hydrophilic region has a contact angle of 60-155 degrees. In some embodiments, the method comprises solubilizing cellular components from more than one region of interest in the planar tissue section. In some embodiments, the method comprises solubilizing cellular components from at least 10, at least 100, at least 1000, or at least 10,000 regions of interest in the planar tissue section. In some embodiments, the hydrophobic mask circumscribing the at least one region of interest in the planar tissue section comprises a grid pattern. In some embodiments, the hydrophobic mask circumscribing the at least one region of interest in the planar tissue section comprises an ellipse. In some embodiments, the hydrophobic mask circumscribing the at least one region of interest in the planar tissue section on a solid substrate is applied to the planar tissue section using a piezoelectric ink-jet delivery device. In some embodiments, the planar tissue section is about 2 to about 50 µm in thickness. In some embodiments, the planar tissue section is about 1 to about 15 µm in thickness. In some embodiments, the planar tissue section is a formalin fixed, paraffin embedded (FFPE) tissue section. In some embodiments, the planar tissue section is an unfixed tissue section.

In some aspects, the present disclosure provides for a system for isolating cellular components from at least one region of interest in a planar tissue section on a first solid support, comprising: (a) the planar tissue section on a first solid support comprising the at least one region of interest circumscribed with a hydrophobic mask; (b) a second solid support comprising at least one agent transfer array element positioned on the surface of the solid substrate so as to align with the at least one region of interest in the planar tissue section, the at least one agent transfer array element including a solution comprising one or more extraction agents; and (c) a motorized stage coupled to the solid support comprising the at least one agent transfer array element and capable of translating the solid support such that the at least one agent transfer array element positioned on the surface of the solid substrate can contact the at least one region of interest in the planar tissue section circumscribed with a hydrophobic mask. In some embodiments, the system comprises a computer system configured to control the position of the motorized stage such that the at least one agent transfer array element positioned on the surface on the second solid substrate contacts the at least one region of interest in the tissue section. In some embodiments, the hydrophobic mask solution is applied by a system comprising (i) a piezoelectric ink-jet delivery device capable of delivering a hydrophobic mask solution to the tissue section on the solid support and (ii) a computer system configured to control the piezoelectric ink-jet delivery device to circumscribe at least one region of interest in the planar tissue section with the hydrophobic mask solution to generate a hydrophobic mask. In some embodiments, the at least one agent transfer array element positioned on the surface of the second solid substrate comprises at least one hydrophilic region circumscribed by a hydrophobic region. In some embodiments, the hydrophobic mask solution comprises at least one of C7F15CH2OCOC(CH3)=CH2, FC-722, PerFluoroCoat, or FluoroPel. In some embodiments, the hydrophobic mask solution comprises at least one of an acrylate or cyanoacrylate. In some embodiments, the at least one agent transfer array element positioned on the surface of the second solid substrate is capable of delivering a volume of solution 10,000 picoliters or less, 1,000 picoliters or less, 500 picoliters or less, 250 picoliters or less, 100 picoliters or less, 50 picoliters or less, 10 picoliters or less, or 2 picoliters or less. In some embodiments, the contact angle of the hydrophobic region circumscribing the at least one hydrophilic region is 60-155 degrees. In some embodiments, the system for hydrophobic mask solution application comprises a UV light source capable of polymerizing said hydrophobic mask solution after application to the planar tissue section. In some embodiments, the system for hydrophobic mask solution application comprises an apparatus for chemical vapor deposition of a perfluoroalkyltrichlorosilane or a perfluoroalkyl silane.

In some aspects, the present disclosure provides for a kit for isolating cellular components from at least one region of interest in a planar tissue section, comprising any of the elements of any one of the aspects of embodiments of any of the methods, systems, or tissue sections described herein.

In some aspects, the present disclosure provides for a tissue section, comprising thereupon from bottom to top at least one cyanoacrylate layer followed by at least one perfluoroalkyl silane layer. In some embodiments, the perfluoroalkyl silane layer comprises a perfluoroalkyltrichlorosilane or a perfluoroalkyltris(dimethylamino)silane. In some embodiments, the perfluoroalkyltrichlorosilane is FOTS. In some embodiments, the tissue section comprises at least one non-silylated fluoroalkyl layer below the at least one cyanoacrylate layer. In some embodiments, the non-silylated fluoroalkyl layer comprises a fluoroacrylate or a non-silylated perfluoroalkane compound. In some embodiments, the perfluoroalkyltrichlorosilane is FOTS ((tridecafluoro-1,1,2,2-tetrahydrooctyl) trichlorosilane). In some embodiments, the tissue section comprises at least one region lacking the cyanoacrylate layer circumscribed by regions possessing the cyanoacrylate layer. In some embodiments, the region is substantially elliptical, polygonal, or free-form. In some embodiments, the application of an aqueous solution of detergent to the tissue section is capable of solubilizing cells within the region. In some embodiments, the region is less than about 1 mm in size. In some embodiments, the region is less than about 100 microns in size.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

Novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 2A, 2B, 2C, 2D, 2E, and 2F show bright field microscope images (2A, 2B, 2C, and 2D are 10×, 2E is 4× magnification) demonstrating regions of interest of varying size (~25 micron, ~100 micron, ~250 micron, 500 micron, and 1 mm diameter) and shape (square or circle) isolated from FFPE human liver microtome sections by application of the hydrophobic masking technique described herein.

FIG. 6 shows example hypothetical data illustrating how application of the hydrophobic masking process of the current disclosure in combination with microscopic analysis and spatially aware tagging can allow for association of gene expression and/or sequence data with particular cell types in the tissue section.

FIG. 7 depicts two stained z-slices of an FFPE breast cancer tissue section (Biomax™, huCAT299) containing cancerous and normal tissue regions. Left shows a hematoxylin and eosin (H&E) stained section; right shows another slice of the same tumor sample stained using immunohistochemistry (IHC) for the cancer marker HER2.

FIG. 8 depicts the chemical masking process described herein applied to various serial sections of the same FFPE breast cancer sample all depicted in FIG. 7. The left image depicts the various masking patterns all applied to the same image, while the right images depict the sections post-application of the chemical mask, demonstrating the regions of tissue that have been selected.

FIG. 9 depicts results of the qPCR analysis performed on samples extracted as shown in FIG. 8 and described in Example 8.

FIGS. 10A and 10B depict a flow diagram illustrating the hydrophobic masking process described in Example 5.

DETAILED DESCRIPTION OF THE INVENTION

Figure 1:
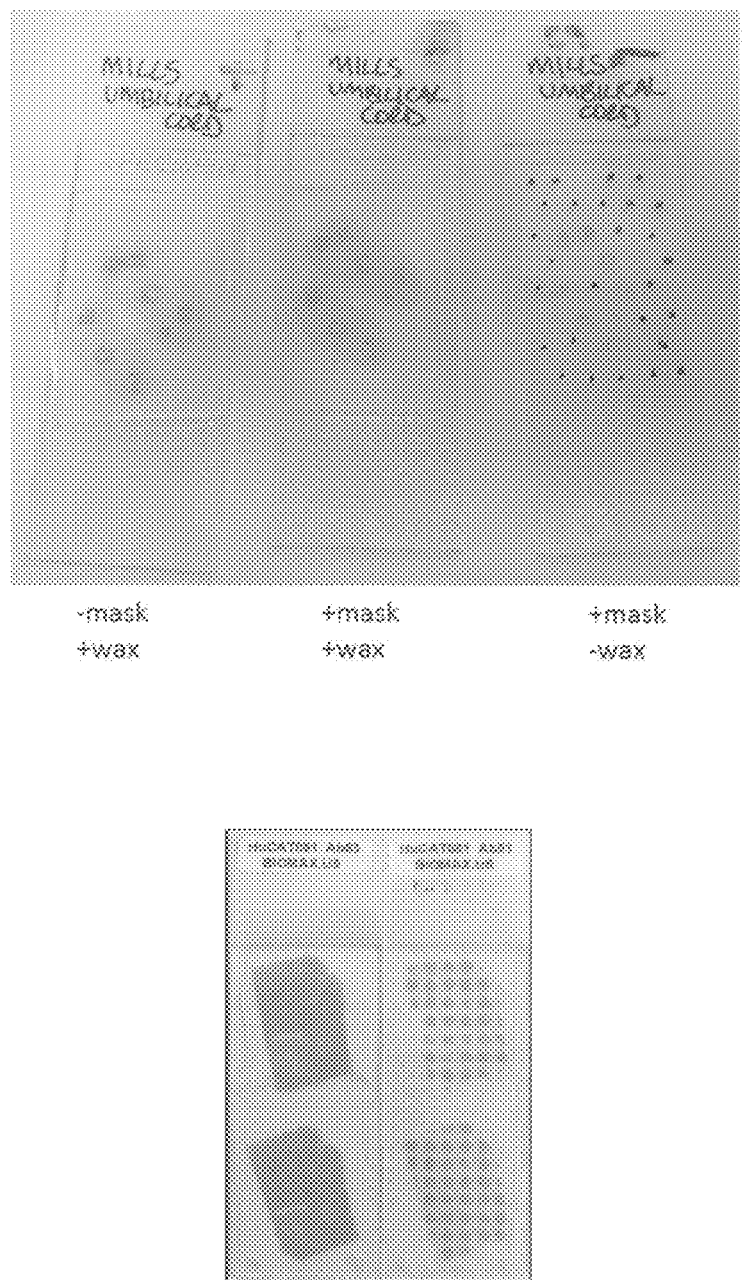
FIG. 1 shows (top) a photograph of hematoxylin/eosin staining of FFPE hepatocellular carcinoma sections without any further treatment (left), and with hydrophobic masking as described herein (right); and (bottom) shows stained microtome liver sections (left) and hydrophobic mask patterned microtome liver section, stained post patterning (right).

Clinical analyses based on detection of rare and or diverse cell types within a tissue are difficult. For example, precancerous tissues may contain only a small proportion of abnormal cells, causing the surrounding normal cells to dilute the signal and stymie early stage detection of cancers. Late stage tumors, in contrast, may have a high population of abnormal cells but may comprise a large diversity of cells with different genotypes that respond differently to chemotherapeutic strategies. In these cases, the ability to selectively isolate and analyze morphologically abnormal cells would be a boon to improved diagnosis and understanding of disease pathophysiology.

However, existing methods of isolation and analysis of small populations of selected cells within tissue samples are laborious, expensive, and unsuited to truly high-throughput multiplex analysis of tissues (e.g. laser capture microdissection, which requires a large amount of manual manipulation and expensive machinery).

Accordingly, there is a need for a straightforward, inexpensive, high-throughput method for multiplex isolation and analysis of regions within tissue samples.

Definitions

The term "tissue" refers to an aggregation of cells, and, optionally, intercellular matter (such as ECM). Typically the cells in a tissue are not free-floating and are attached to each other to form a multicellular structure. Tissue types include, but are not limited to, muscle, nerve, epidermal and connective tissues. Tissues as described herein may be derived from a variety of organisms, including but not limited a mammal such as a rodent, mouse, rat, rabbit, guinea pig, ungulate, horse, sheep, pig, goat, cow, cat, dog, primate (i.e. human or non-human primate); a plant such as *Arabidopsis thaliana*, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish; a reptile; or an amphibian such as a frog or *Xenopus laevis*.

The term "contact angle" refers to the shape of a liquid droplet resting on a solid surface. With the assumption that there is a liquid on a solid plane in air, the term "contact angle" indicates the angle between the tangent line of the liquid and the tangent line of the solid plane at a contact point of the liquid, the solid plane, and the air.

The term "hydrophobic" refers to a surface or coating that is difficult to wet with water. A surface would be considered hydrophobic if it demonstrated a receding water contact angle of at least 60°, very hydrophobic if it demonstrated a contact angle of a least 110°, and extremely hydrophobic if it demonstrated a receding water contact angle of at least 1200.

The term "superhydrophobic" refers to a surface or coating that is extremely difficult to wet with water. A superhydrophobic surface or coating will usually have contact angles in excess of 140°, and often in excess of 150°.

The term "hydrophilic" is used to refer to surfaces that are wettable by aqueous fluids. A surface is said to be wetted by a fluid (hydrophilic) when the fluid tends to spread spontaneously across the surface as opposed to forming discrete droplets. A surface would be considered hydrophilic if it demonstrated contact angle of less than about 50 degrees.

"Inkjet delivery" is a non-contact approach that enables processing of 1-100 picoliter (pl) droplets of liquid into two-dimensional and three dimensional structures. This approach involves dissolving or dispersing the material of interest in a liquid in order to form an ink. The most popular method used for ink-jet delivery is the Droplet-on-Demand (DOD) method, wherein drops are ejected from a micrometer-scale nozzle are created by either (a) heating of the liquid to a temperature greater than the boiling temperature (thermal DOD) to generate a vapor bubble that stimulates release of droplets from the nozzle or (b) application of a voltage to a piezoelectric transducer, which leads to vibration of the material and release of droplets from the nozzle (piezoelectric DOD).

Overview

Provided herein is a method of isolating cellular components from at least one region of interest in a planar tissue section on a solid substrate. The method is in-situ, and does not require the pre-preparation of immobilized nucleotide arrays to define regions from tissue. Rather, the method involves in-situ preparation of a hydrophobic mask on a tissue section to isolate regions of interest, followed by the optional use of a surface tension array to add and/or remove extraction and/or analysis reagents from particular regions of interest circumscribed by the hydrophobic mask. Use of the surface tension array is particularly useful e.g. in the case when there are a large number (e.g. greater than 10, greater than 100, greater than 1000) of regions isolated by the hydrophobic mask. In some embodiments, the method involves (a) applying to the planar tissue section a hydrophobic mask circumscribing the at least one region of interest in the planar tissue section on a solid substrate; (b) dispensing a solution comprising one or more extraction agents onto an agent transfer device comprising at least one agent transfer array element positioned on a surface of a second solid substrate; and (c) contacting the at least one agent transfer array element positioned on the surface of the second solid substrate to the planar tissue section, such that the at least one agent transfer array element spatially corresponds to the at least one region of interest in the planar tissue section. In some embodiments, the contacting allows the solution comprising the one or more extraction agents to be transferred to the at least one region of interest in the planar tissue section, thereby solubilizing the cellular components in the at least one region of interest in the solution comprising the one or more extraction agents.

The solution comprising the one or more extraction agents may include one or more tags or labels suitable for labeling nucleic acids or proteins. Such tags or labels may include a barcode or otherwise be spatially addressable such that nucleic acid sequencing data or mass spectrometry data derived from extracted nucleic acids or proteins can subsequently be associated with the region of interest they were isolated from. As such, the methods herein also provide a scheme for spatially tagging nucleic acids or proteins from a tissue section.

Tissue Section

The tissue section utilized in the method can be prepared by any standard method commonly used for immunohistochemical preparations, and may be either fixed or unfixed (e.g. freshly excised, or prepared by a non-fixing tissue preparation method such as freezing). Fixation of cells or tissue may involve the use of cross-linking agents, such as formaldehyde, glutaraldehyde, and the like.

Fixed tissue can further be embedded in paraffin wax or a hydrogel (such as a polyacrylamide support matrix). A popular method of tissue preparation is FFPE (Formalin-fixed, Paraffin-embedded), which involves fixing tissue pieces in formalin solution, dehydrating the tissue in progressively higher concentrations of alcohol, clearing the tissue with xylene, infiltrating the tissue with wax (typically paraffin, a mixture of straight chain or n-alkanes with a carbon chain length of between 20 and 40 that can be obtained with various different melting points), and then embedding the tissue in a wax block. FFPE tissues can then be prepared into tissue sections using a microtome.

In some embodiments, thicknesses of tissue sections prepared by FFPE are about 1 micron to about 50 microns.

In some embodiments, thicknesses of tissue sections prepared by FFPE are at least about 1 micron. In some embodiments, thicknesses of tissue sections prepared by FFPE are at most about 50 microns. In some embodiments, thicknesses of tissue sections prepared by FFPE are about 1 micron to about 3 microns, about 1 micron to about 5 microns, about 1 micron to about 10 microns, about 1 micron to about 15 microns, about 1 micron to about 20 microns, about 1 micron to about 30 microns, about 1 micron to about 40 microns, about 1 micron to about 50 microns, about 3 microns to about 5 microns, about 3 microns to about 10 microns, about 3 microns to about 15 microns, about 3 microns to about 20 microns, about 3 microns to about 30 microns, about 3 microns to about 40 microns, about 3 microns to about 50 microns, about 5 microns to about 10 microns, about 5 microns to about 15 microns, about 5 microns to about 20 microns, about 5 microns to about 30 microns, about 5 microns to about 40 microns, about 5 microns to about 50 microns, about 10 microns to about 15 microns, about 10 microns to about 20 microns, about 10 microns to about 30 microns, about 10 microns to about 40 microns, about 10 microns to about 50 microns, about 15 microns to about 20 microns, about 15 microns to about 30 microns, about 15 microns to about 40 microns, about 15 microns to about 50 microns, about 20 microns to about 30 microns, about 20 microns to about 40 microns, about 20 microns to about 50 microns, about 30 microns to about 40 microns, about 30 microns to about 50 microns, or about 40 microns to about 50 microns. In some embodiments, thicknesses of tissue sections prepared by FFPE are about 1 micron, about 3 microns, about 5 microns, about 10 microns, about 15 microns, about 20 microns, about 30 microns, about 40 microns, or about 50 microns.

Embedded tissue sections can be de-paraffinized prior to further processing (such as processing with the hydrophobic chemistry and sample extraction techniques further described herein). De-paraffinization can be performed, e.g. by incubation of the section in a xylene bath, followed by incubation in a xylene/ethanol bath, followed by incubation in baths of progressively lower ethanol concentration (from 100%-50%), followed by drying or rinsing in water.

In some embodiments, unfixed or fixed tissue can be prepared into sections by cryosectioning. For unfixed tissue, tissue is first immersed in a frozen tissue matrix (e.g. OCT or Cryomatrix), frozen in an isopentane and/or 2-methylbutane bath in contact with liquid nitrogen, and sectioned on a cryostat. For fixed tissue, tissue can be cryoprotected in sucrose prior to embedding/freezing in tissue matrix, which involves incubation in progressively higher concentration sucrose baths (up to 30%). The cryoprotected fixed tissue can then be immersed in frozen tissue matrix (e.g. OCT or Cryomatrix) and can be frozen in a) an isopentane bath in contact with liquid nitrogen, or b) an alternate slower freezing method (e.g. powdered dry ice or a dry-ice methanol/ethanol slurry). Cryoprotected frozen fixed tissue can then be sectioned on a cryostat.

In some embodiments, thickness of tissue sections prepared by cryosectioning can be about 5 microns to about 50 microns. In some embodiments, thickness of tissue sections prepared by cryosectioning can be at least about 5 microns. In some embodiments, thickness of tissue sections prepared by cryosectioning can be at most about 50 microns. In some embodiments, thickness of tissue sections prepared by cryosectioning can be about 5 microns to about 7 microns, about 5 microns to about 9 microns, about 5 microns to about 11 microns, about 5 microns to about 13 microns, about 5 microns to about 15 microns, about 5 microns to about 20 microns, about 5 microns to about 30 microns, about 5 microns to about 40 microns, about 5 microns to about 50 microns, about 7 microns to about 9 microns, about 7 microns to about 11 microns, about 7 microns to about 13 microns, about 7 microns to about 15 microns, about 7 microns to about 20 microns, about 7 microns to about 30 microns, about 7 microns to about 40 microns, about 7 microns to about 50 microns, about 9 microns to about 11 microns, about 9 microns to about 13 microns, about 9 microns to about 15 microns, about 9 microns to about 20 microns, about 9 microns to about 30 microns, about 9 microns to about 40 microns, about 9 microns to about 50 microns, about 11 microns to about 13 microns, about 11 microns to about 15 microns, about 11 microns to about 20 microns, about 11 microns to about 30 microns, about 11 microns to about 40 microns, about 11 microns to about 50 microns, about 13 microns to about 15 microns, about 13 microns to about 20 microns, about 13 microns to about 30 microns, about 13 microns to about 40 microns, about 13 microns to about 50 microns, about 15 microns to about 20 microns, about 15 microns to about 30 microns, about 15 microns to about 40 microns, about 15 microns to about 50 microns, about 20 microns to about 30 microns, about 20 microns to about 40 microns, about 20 microns to about 50 microns, about 30 microns to about 40 microns, about 30 microns to about 50 microns, or about 40 microns to about 50 microns. In some embodiments, thickness of tissue sections prepared by cryosectioning can be about 5 microns, about 7 microns, about 9 microns, about 11 microns, about 13 microns, about 15 microns, about 20 microns, about 30 microns, about 40 microns, or about 50 microns.

Chemical Mask

A. Composition/Application

In some embodiments, the methods involved herein involve the deposition of a chemical mask to surround and isolate regions of interest in tissue sections (e.g. fresh frozen, fixed frozen, and/or deparaffinized FFPE tissue sections). The chemical mask allows the selective aqueous extraction/rehydration of cellular components from regions of interest without contamination by components of surrounding regions (as regions of the sample other than the region of interest repel solution needed to disrupt/extract/rehydrate cells). As such, the chemical mask solution is hydrophobic (e.g. has a receding water contact angle of at least 60 degrees).

In some embodiments, the contact angle of the chemical mask can be about 60 degrees to about 150 degrees. In some embodiments, the contact angle of the chemical mask can be at least about 60 degrees. In some embodiments, the contact angle of the chemical mask can be at most about 150 degrees. In some embodiments, the contact angle of the chemical mask can be about 60 degrees to about 100 degrees, about 60 degrees to about 110 degrees, about 60 degrees to about 140 degrees, about 60 degrees to about 150 degrees, about 100 degrees to about 110 degrees, about 100 degrees to about 140 degrees, about 100 degrees to about 150 degrees, about 110 degrees to about 140 degrees, about 110 degrees to about 150 degrees, or about 140 degrees to about 150 degrees. In some embodiments, the contact angle of the chemical mask can be about 60 degrees, about 100 degrees, about 110 degrees, about 140 degrees, or about 150 degrees.

A wide variety of surface-coating polymers and copolymers have been described which can be used to generate a surface receding water contact angle of at least 60 degrees and are thus suitable for use in generating a chemical mask as described herein.

An important class of such agents is fluorocarbons, especially fluorinated carbon monomers at least one terminal trifluoromethyl group. In some embodiments, the fluorinated carbon monomers containing at least one terminal trifluoromethyl group contain from about 3 to about 20 carbon atoms. In some embodiments, such fluorocarbons are substantially non-branched fluoroalkyl or perfluoroalkyl ethylenically unsaturated monomers. In some embodiments the ethylenically unsaturated monomer is an acrylate, such as a methacrylate. In some embodiments the ethylenically unsaturated monomer is a cyanoacrylate. In some embodiments, fluorinated carbon monomers containing at least one terminal trifluoromethyl group are fluorinated or perfluorinated acrylates, silicones, epoxies, urethanes, or oximes, or any combination thereof. Such agents include fluoroacrylates (or solutions thereof) or perfluoroalkylsilanes. Fluoroacrylates or solutions thereof include, but are not limited to, the fluoroalkyl methacrylate monomer C7F15CH2COC(CH3)=CH2, FC-722 (available from 3M), PerFluoroCoat (Cytonix), and FluoroPel (Cytonix, including but not limited to the the FluoroPel 800 and 800M products). The solutions can be used full strength but may be diluted with a solvent (e.g. a fluorosolvent, an alcohol, ethanol) to form low concentrations of coating polymer or fluoroalkane. The polymer solution used to make the coatings of the invention preferably have a coating polymer content of from about 0.01% by weight to about 50% by weight. Perfluoroalkylsilanes include perfluoroalkyltrichlorosilanes and perfluorotris(dimethylamino)silanes (e.g. PF10TAS). Perfluoroalkyltrichlorosilanes are organic molecules comprising a trichlorosilyl group attached to perfluorinated alkyl groups of varying length and isomerism (e.g. C1-C20 perfluoroalkyl groups such as perfluoromethyl, perfluoroethyl, perfluoropropyl, perfluorobutyl, perfluoro-tertbutyl, perfluoropentyl, perfluorohexyl, perfluorooctyl, perfluorononyl, perfluorodecyl). Examples of perfluoroalkyltrichlorosilanes include, but are not limited to FOTS (Trichloro(1H,1H,2H,2H-perfluorooctyl)silane), Trichloro((1H,1H,2H,2H-perfluorodecyl trichlorosilane, and 1H,1H,2H,2H-Perfluorododecyltrichlorosilane. Perfluorotris(dimethylamino)silanes are organic molecules comprising a tris(dimethylamino)silyl group attached to perfluorinated alkyl groups of varying length and isomerism (e.g. C1-C20 perfluoroalkyl groups such as perfluoromethyl, perfluoroethyl, perfluoropropyl, perfluorobutyl, perfluoro-tertbutyl, perfluoropentyl, perfluorohexyl, perfluorooctyl, perfluorononyl, perfluorodecyl). Perfluoroalkylsilanes, perfluorotris(dimethylamino)silanes or perfluoroalkyltrichlorosilanes may be applied directly (e.g. dipping, spraying) or indirectly (e.g. chemical vapor deposition, CVD).

In some embodiments, the fluorocarbon is applied directly as a polymer (either selectively to a region desired to be excluded, or nonspecifically to the entire tissue area) to the tissue section to generate the mask (e.g., fluorinated carbon monomer such as a fluoroacrylate is added to the tissue section along with photoinitiator). In some embodiments, the fluorocarbon is applied to the tissue section following an initial application, for example by inkjet printing, of non-fluorinated acrylate or cyanoacrylate along with photoinitiator to the tissue section). In some embodiments, more than one fluorocarbon is applied to the tissue section as a copolymer (e.g. an initial application of a fluorocarbon such as a fluoroacryate to the tissue section, followed by application of non-fluorinated acrylate or cyanoacrylate along with photoinitiator thereon, followed by application of the same fluorocarbon or a different fluorocarbon such as a perfluoroalkylsilane thereon).

In some embodiments, the fluorocarbon is applied as a polymer to a layer of hydrophobic material atop the tissue section to generate the mask (e.g. following an initial application, for example by spraying or dipping, of a hydrophobic polymer such as cyanoacrylate to the tissue section). In some embodiments, the fluorocarbon is applied to the layer of hydrophobic material, with the same or a different pattern as the layer of hydrophobic material, such that the fluorocarbon and hydrophobic material form a copolymer mask where they meet.

In some embodiments, a layer of hydrophobic material is applied as a polymer to the chemical mask (e.g. following initial application of the mask material as a polymer or copolymer to the tissue section). In some embodiments, the hydrophobic material is a fluorocarbon. In some embodiments the hydrophobic material comprises a perfluoroalkylsilane such as a perfluoroalkyltrichlorosilane or a perfluoroalkyltris(dimethylamino)silane (tridecafluoro-1,1,2,2-tetrahydrooctyl)trichlorosilane. In some embodiments, the hydrophobic material comprises a fluorocarbon. In some embodiments the hydrophobic material comprises a perfluoroalkyltrichlorosilane such as trichloro(1H,1H,2H,2H-perfluorooctyl)silane. In some embodiments, the hydrophobic material comprises a perfluoroalkyltris(dimethylamino)silane such as PF10TAS.

Other classes of agents that can be applied to generate a chemical mask include acrylates and cyanoacrylates that are photo-curable (can be cured with UV)—with or without a photo-catalyst.

Monomers composing the chemical mask can be applied to the tissue section by a variety of approaches, including but not limited to ink-jet printing (e.g. DOD or piezoelectric inkjet printing methods) using the monomer suspended in a suitable solvent (e.g. an alcohol such as ethanol, propylene glycol, propylene glycol monomethyl ether acetate, methyl ethyl ketone, or suitable fluorocarbons with boiling points above room temperature such as perfluorooctane, perfluoro-2-methylpentane, perfluoro-1,3-dimethylcyclohexane, perfluorodecalin, 1,3-difluoropropane, and the like).

The chemical mask can comprise one or more monomer or polymer layers. The one or more monomer or polymer layers can comprise the same or different monomer or polymer. The one or more monomer or polymer layers can form a copolymer. The one or more monomer or polymer layers can be one, two, three, four, five, six, seven, eight, nine, or ten polymer layers, or more. In some embodiments, the chemical mask comprises a layer of cyanoacrylate followed by a layer of perfluoroalkylsilane (e.g. perfluoroalkyltrichlorosilane or perfluoroalkyltris(dimethylamino)silane). In some embodiments, the chemical mask comprises multiple layers of cyanoacrylate followed by perfluoroalkylsilane (e.g. perfluoroalkyltrichlorosilane or perfluoroalkyltris(dimethylamino)silane). In some embodiments, the chemical mask comprises a layer of fluoroacrylate or non-silylated fluoroalkane followed by a layer of cyanoacrylate, followed by a layer of perfluoroalkylsilane (e.g. perfluoroalkyltrichlorosilane or perfluoroalkyltris(dimethylamino)silane). In some embodiments, the chemical mask comprises multiple layers of fluoroacrylate or non-silylated fluoroalkane followed by cyanoacrylate followed by perfluoroalkylsilane (e.g. perfluoroalkyltrichlorosilane or perfluoroalkyltris(dimethylamino)silane).

B. Circumscribed Region of Interest Format (Shape, Size, #, Separation, Array, Preselected ROI, Association with Previous Image)

The chemical mask can be used to circumscribe at least one region of interest on the tissue section for subsequent isolation, which can be a range of shapes and sizes. The region of interest can be a variety of shapes, such as square, circular, ovular, triangular, trapezoidal, pentagonal, hexagonal, or n-polyhedral. The region of interest can be about 176 square microns to about 780,000 square microns. The region of interest can be at least about 176 square microns. The region of interest can be at most about 780,000 square microns. The region of interest can be about 176 square microns to about 12,000 square microns, about 176 square microns to about 49,000 square microns, about 176 square microns to about 190,000 square microns, about 176 square microns to about 780,000 square microns, about 12,000 square microns to about 49,000 square microns, about 12,000 square microns to about 190,000 square microns, about 12,000 square microns to about 780,000 square microns, about 49,000 square microns to about 190,000 square microns, about 49,000 square microns to about 780,000 square microns, or about 190,000 square microns to about 780,000 square microns. The region of interest can be about 176 square microns, about 12,000 square microns, about 49,000 square microns, about 190,000 square microns, or about 780,000 square microns. The region of interest can be about 490 square microns to about 780,000 square microns. The region of interest can be at least about 490 square microns. The region of interest can be at most about 780,000 square microns. The region of interest can be about 490 square microns to about 12,000 square microns, about 490 square microns to about 49,000 square microns, about 490 square microns to about 190,000 square microns, about 490 square microns to about 780,000 square microns, about 12,000 square microns to about 49,000 square microns, about 12,000 square microns to about 190,000 square microns, about 12,000 square microns to about 780,000 square microns, about 49,000 square microns to about 190,000 square microns, about 49,000 square microns to about 780,000 square microns, or about 190,000 square microns to about 780,000 square microns. The region of interest can be about 490 square microns, about 12,000 square microns, about 49,000 square microns, about 190,000 square microns, or about 780,000 square microns.

A circular region of interest can be about 15 microns in diameter to about 10,000 square microns in diameter. A circular region of interest can be at least about 15 microns in diameter. A circular region of interest can be at least about 25 microns in diameter. A circular region of interest can be at most about 1,000 microns in diameter. A circular region of interest can be about 15 microns in diameter to about 50 microns in diameter, about 15 microns in diameter to about 125 microns in diameter, about 15 microns in diameter to about 250 microns in diameter, about 15 microns in diameter to about 500 microns in diameter, about 15 microns in diameter to about 750 microns in diameter, about 15 square microns in diameter to about 1,000 microns in diameter, about 15 microns in diameter to about 125 microns in diameter, about 50 microns in diameter to about 250 microns in diameter, about 50 microns in diameter to about 500 microns in diameter, about 50 microns in diameter to about 750 microns in diameter, about 50 microns in diameter to about 1,000 microns in diameter, about 125 microns in diameter to about 250 microns in diameter, about 125 microns in diameter to about 500 microns in diameter, about 125 microns in diameter to about 750 microns in diameter, about 125 microns in diameter to about 1,000 microns in diameter, about 250 microns in diameter to about 500 microns in diameter, about 250 microns in diameter to about 750 microns in diameter, about 250 microns in diameter to about 1,000 microns in diameter, about 500 microns in diameter to about 750 microns in diameter, about 500 microns in diameter to about 10,000 microns in diameter, or about 750 microns in diameter to about 1,000 microns in diameter. A circular region of interest can be about 15 microns in diameter, about 25 microns in diameter, about 50 microns in diameter, about 125 microns in diameter, about 250 microns in diameter, about 500 microns in diameter, about 750 microns in diameter, about 1,000 microns in diameter, about 2,000 microns in diameter, about 3,000 microns in diameter, about 4,000 microns in diameter, about 5,000 microns in diameter, about 6,000 microns in diameter, about 7,000 microns in diameter, about 8,000 microns in diameter, about 9,000 microns in diameter, or about 10,000 microns in diameter. A circular region of interest can be less than or equal to about 15 microns in diameter, less than or equal to about 25 microns in diameter, less than or equal to about 50 microns in diameter, less than or equal to about 125 microns in diameter, less than or equal to about 250 microns in diameter, less than or equal to about 500 microns in diameter, less than or equal to about 750 microns in diameter, less than or equal to about 1,000 microns in diameter, less than or equal to about 2,000 microns in diameter, less than or equal to about 3,000 microns in diameter, less than or equal to about 4,000 microns in diameter, less than or equal to about 5,000 microns in diameter, less than or equal to about 6,000 microns in diameter, less than or equal to about 7,000 microns in diameter, less than or equal to about 8,000 microns in diameter, less than or equal to about 9,000 microns in diameter, or less than or equal to about 10,000 microns in diameter.

In some embodiments, more than one region of interest is circumscribed in a tissue sample such that the regions of interest form a grid. In some embodiments, the grid comprises about 10 regions of interest to about 10,000 regions of interest. In some embodiments, the grid comprises at least about 10 regions of interest. In some embodiments, the grid comprises at most about 10,000 regions of interest. In some embodiments, the grid comprises about 10 regions of interest to about 100 regions of interest, about 10 regions of interest to about 1,000 regions of interest, about 10 regions of interest to about 10,000 regions of interest, about 100 regions of interest to about 1,000 regions of interest, about 100 regions of interest to about 10,000 regions of interest, or about 1,000 regions of interest to about 10,000 regions of interest. In some embodiments, the grid comprises about 10 regions of interest, about 100 regions of interest, about 1,000 regions of interest, or about 10,000 regions of interest.

In some embodiments, the size, shape, and/or pattern of the region(s) of interest can be user-defined. Such a user-defined pattern can be achieved by first staining/imaging a corresponding tissue section from a higher or lower vertical position in the tissue block by a suitable visualization technique (e.g. hematoxylin/eosin staining, immunofluorescence, immunohistochemistry), defining the regions of interest on the tissue image in a computer system, and transferring the desired pattern to a fresh unprocessed corresponding tissue section using inkjet printing and the guidance of the computer system.

Extraction

A. Solutions

Following definition of one or more region of interest on the tissue section via application of the chemical mask, extraction solutions may be transferred to the one or more region of interest to isolate nucleic acids and/or proteins from the region of interest. Extraction solutions can comprise one or more ionic or nonionic surfactants (e.g., beta-octylglucoside, Triton™-X-100, SDS, Tween™-20, CHAPS), proteases (e.g., Proteinase-K, Trypsin, Chymotrypsin, Lys-C, Asp-N, Collagenase), tonicity adjusting agents (e.g., Dextrose, Glycerol, Mannitol, Potassium Chloride, Sodium Chloride), chaotropes (e.g., Urea, Thiourea, Guanidinium Chloride), nucleases (DNAse, RNAse), buffers (e.g., Tris, Trizma, MOPS, Sodium Phosphate, Bicarbonate, Bicine, CAPS, CAPSO, Tricine, HEPES, MOPSO), protease inhibitors (e.g., AEBSF-HCl, Aprotenin, Bestatin, E-64d, Leupeptin, Pepstatin, EDTA, PMSF), phosphatase inhibitors (e.g. Sodium Fluoride, Sodium Orthovanadate, beta-Glycerophosphase, Sodium Orthophosphate), or nuclease inhibitors (e.g. EDTA, EGTA, DEPC, RNaisin). In the case of frozen unfixed tissue sections, standard compositions for isolation of nucleic acids or proteins from cultured mammalian cells may be used (e.g. solutions containing a buffer, salt, and a surfactant). For the retrieval of protein or DNA from FFPE tissue sections, exemplary protocols can be found, for e.g. in Pikor et al. J Vis Exp. 2011; (49): 2763 or in Paulo et al. JOP. 2013 July; 14(4): 405-414.

i. Soluble Tags

In some embodiments, the extraction solution can further comprise a soluble tag that corresponds spatially to the region of interest, such that downstream multiplex sequencing or mass spectrometry data can be assigned to the region of interest.

For multiplex sequencing (e.g. NGS sequencing) of nucleic acids (e.g. mRNA, cDNA, genomic DNA) derived from the region of interest, suitable soluble tags include synthetic oligonucleotides. Such oligonucleotides comprise a positional sequence (e.g. a nonrandom sequence corresponding to the region of interest) and, optionally, a unique molecular identifier (UMI) which allows for counting of each individual reverse transcribed cDNA molecule in downstream sequencing. The UMI sequences may be generated using random sequence generation. The UMI sequences may be followed by stringent filtering by mapping to the genomes of all common reference species and with pre-set Tm intervals, GC content and a defined distance of difference to the other barcode sequences to ensure that the barcode sequences will not interfere with the capture of the nucleic acid, e.g. RNA from the tissue sample and will be distinguishable from each other without difficulty. The synthetic oligonucleotides may include positional and/or UMI sequences for tagging of just 5' or 3' end-labeling or both 5' and 3' end-labeling of reverse-transcribed cDNA.

Tagging of the nucleic acids (e.g. RNA) isolated from each region of interest using such synthetic oligonucleotides can be accomplished by a variety of methods. In some embodiments, the synthetic oligonucleotides comprising the positional/UMI sequences are double-stranded (optionally hairpin or Y-shaped, and/or optionally including a 3' end T-overhang, as e.g. in Wei et al. Genetics. 2016 January; 202(1): 37-44), and are attached to either end of cDNA generated from first-round reverse transcriptase synthesis using oligo-dT universal primers by A-tailing followed by ligation. In some embodiments, the synthetic oligonucleotides are single stranded and additionally comprise an oligo-dT sequence, such that the positional/UMI sequences are incorporated during first-round reverse transcription into cDNA. Other exemplary primer designs and protocols for cDNA library tagging can be found e.g. in Hashimshony et al. Genome Biology (2016) 17:77, Hashimony et al. Cell Rep. 2012 Sep. 27; 2(3):666-73, and Head et al. Biotechniques. 2014; 56(2): 61-passim.

For multiplex mass spectrometry (e.g. LC-MS/MS) of proteins derived from the one or more region of interest, suitable soluble tags include tandem mass tags available from Thermo Scientific (e.g. Duplex TMT, Simplex TMT, 10plex TMT, 11plex TMT) and those described in WO2016196994A1. These are amine-reactive tags suitable for conjugation to tryptic peptides produced from proteins from the region of interest with slight differences in molecular weight which allow for tryptic peptides originating from multiple distinct samples to be readily distinguished on MS/MS spectra (for further details of TMT construction and detection, see WO2016196994A1 and Zhang et al. Methods Mol Biol. 2017; 1550:185-198).

B. Agent Transfer Device

Figure 3:
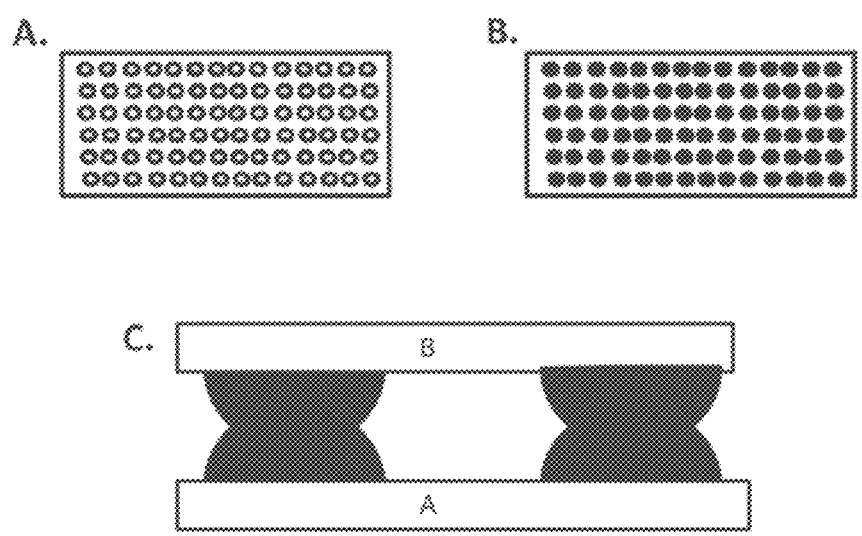
FIG. 3 shows a schematic of how an agent transfer array device (B) can be used to transfer solution to regions of interest on a tissue section (A) by surface tension contact (C).
Figure 4:
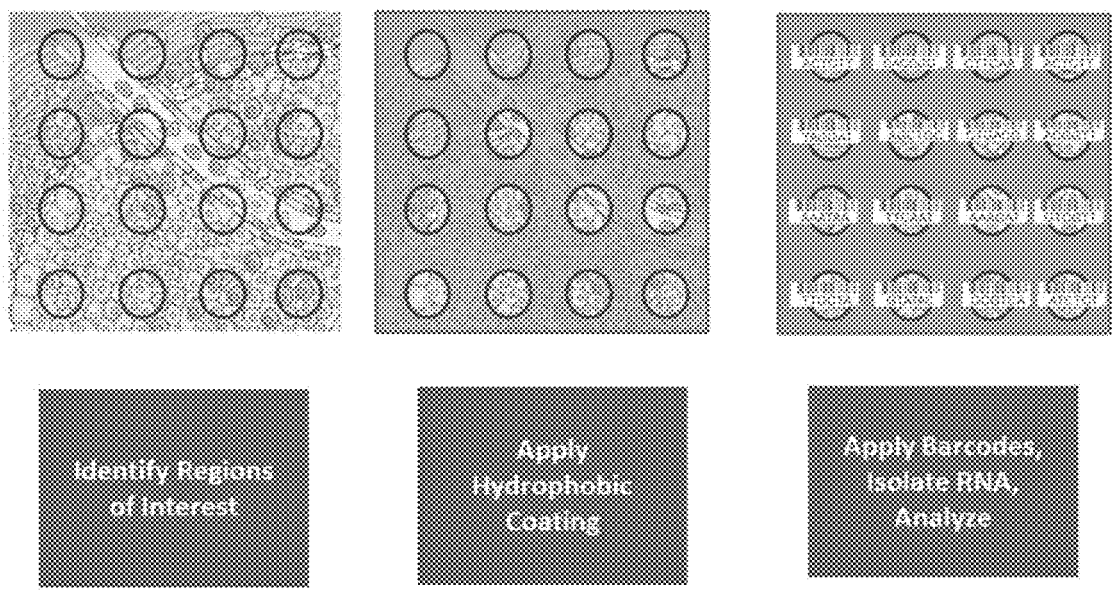
FIG. 4 shows a schematic demonstrating how the hydrophobic masking process allows for isolation and tagging of regions of interest from a tissue section without specialized equipment such as microfluidics or lasers.
Figure 5:
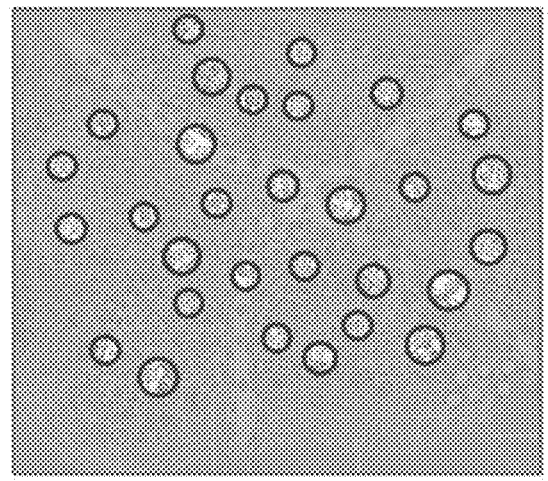
FIG. 5 shows an illustration demonstrating how the hydrophobic masking process allows for delineation of custom regions of interest in a tissue section.
Figure 10A:
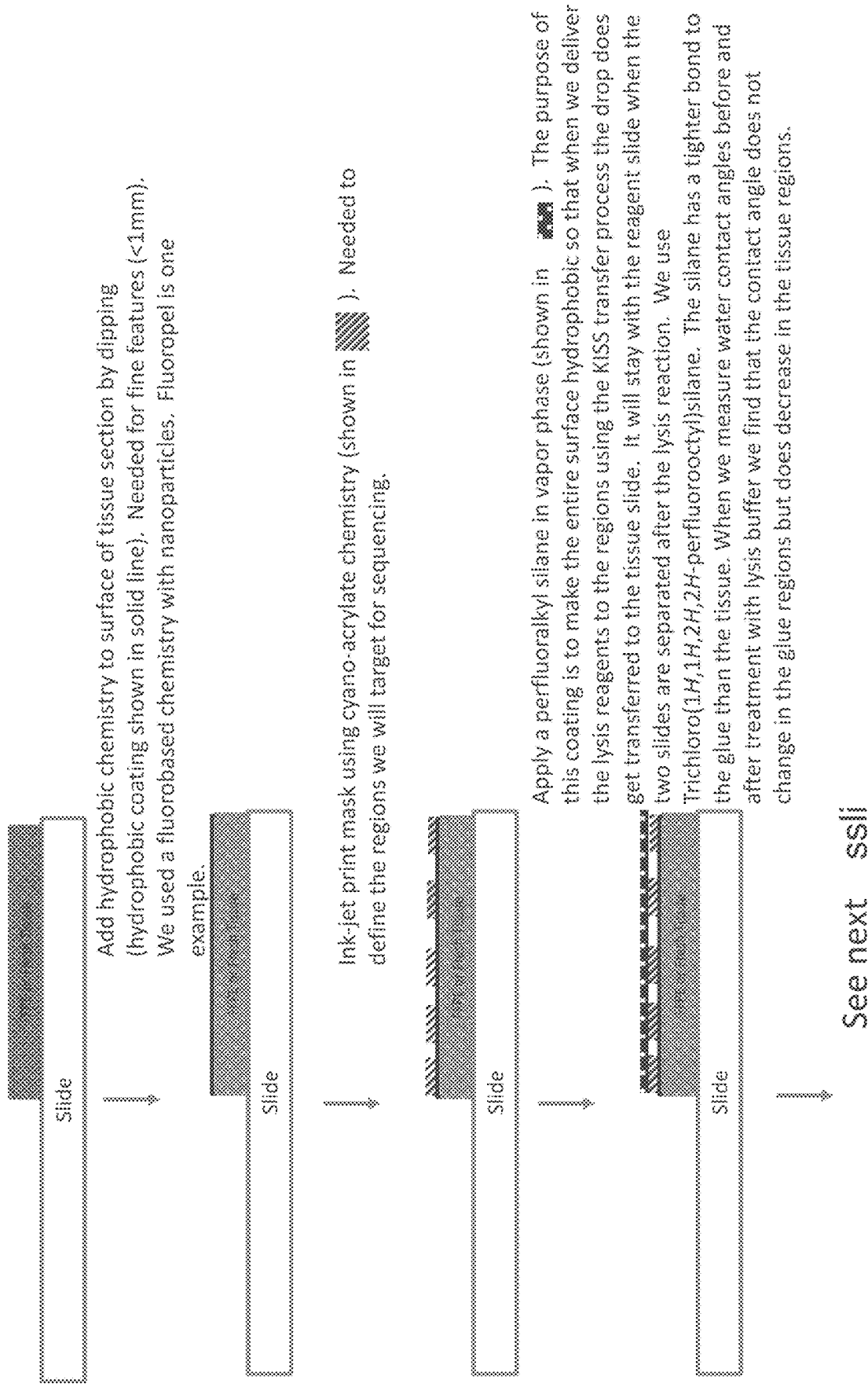

In some embodiments, transfer of extraction solutions or other components to or from the regions of interest on the mask-treated tissue section involves use of one or more agent transfer devices. The agent transfer device comprises an array comprising a plurality of hydrophilic regions (agent transfer array elements) which correspond spatially to the regions of interest on the masked tissue section. The hydrophobic-bordered hydrophilic regions represent a "surface tension array", wherein aqueous solution added to the hydrophilic regions is contained by the bordering hydrophobic regions, and wherein the maximum solution volume of the agent transfer array elements can be controlled by modifying the area/diameter of the hydrophilic regions (controlling the "width" of solution that can be added to the features) and the differential between the contact angle of the hydrophilic region and the hydrophobic region (controlling the "height" of solution that can be added to the features). FIG. 3 demonstrates how an agent transfer array B charged with extraction solution (black) can be used to transfer solution to regions of interest on slide A by contacting the liquid domes of B onto the tissue section and allowing surface tension to draw the liquid meniscus onto the tissue section (C).

Such agent transfer devices can be generated using a variety of different hydrophobic/hydrophilic chemistries on a variety of substrates. One convenient process involves derivatization of glass with a hydrophilic compound, followed by protection of hydrophilic features with a positive photoresist in conjunction with coating using a fluorocarbon. In one embodiment, an array containing hydrophilic agent transfer array features is generated by derivatization of quantitatively clean glass slides a monofunctional (one attachment site for silanation) organosilane such as 3-aminopropyldimethylethoxysilane (APDMS) followed by protection of agent transfer array elements/hydrophilic regions with positive photoresist and treatment with a perfluoroalkyltrichlorosilane such as (tridecafluoro-1,1,2,2-tetrahydrooctyl)trichlorosilane or another suitable anti-stiction coating (e.g. dimethyldichlorosilane DDMS, perflurodecyltris(dimethylamino)silane PF10TAS, perfluorodecanoic acid PFDA, or variants thereof with perfluoroalkyl chains of varying length and isomerism; see e.g. Ashurst et al. IEEE Transactions on Device and Materials Relatability. 3(4):173-178 (2003)). Further chemical details of derivatization of glass slides with hydrophilic and hydrophobic regions can be found, for e.g., in Butler et al. J. Am. Chem. Soc. 2001, 123, 8887-8894 and US20150268233 A1.

The dimension of the hydrophilic regions/agent transfer array element on the agent transfer device correspond to the dimensions of the region of interest masked on the tissue sample. The agent transfer array element can be a variety of shapes, such as square, circular, ovular, triangular, trapezoidal, pentagonal, hexagonal, or n-polyhedral. The agent transfer array element can be about 490 square microns to about 780,000 square microns. The agent transfer array element can be at least about 490 square microns. The agent transfer array element can be at most about 780,000 square microns. The agent transfer array element can be about 490 square microns to about 12,000 square microns, about 490 square microns to about 49,000 square microns, about 490 square microns to about 190,000 square microns, about 490 square microns to about 780,000 square microns, about 12,000 square microns to about 49,000 square microns, about 12,000 square microns to about 190,000 square microns, about 12,000 square microns to about 780,000 square microns, about 49,000 square microns to about 190,000 square microns, about 49,000 square microns to about 780,000 square microns, or about 190,000 square microns to about 780,000 square microns. The agent transfer array element can be about 490 square microns, about 12,000 square microns, about 49,000 square microns, about 190,000 square microns, or about 780,000 square microns. A circular agent transfer array element can be about 25 square microns in diameter to about 1,000 square microns in diameter. A circular agent transfer array element can be at least about 25 square microns in diameter. A circular agent transfer array element can be at most about 1,000 square microns in diameter. A circular agent transfer array element can be about 25 square microns in diameter to about 50 square microns in diameter, about 25 square microns in diameter to about 125 square microns in diameter, about 25 square microns in diameter to about 250 square microns in diameter, about 25 square microns in diameter to about 500 square microns in diameter, about 25 square microns in diameter to about 750 square microns in diameter, about 25 square microns in diameter to about 1,000 square microns in diameter, about 50 square microns in diameter to about 125 square microns in diameter, about 50 square microns in diameter to about 250 square microns in diameter, about 50 square microns in diameter to about 500 square microns in diameter, about 50 square microns in diameter to about 750 square microns in diameter, about 50 square microns in diameter to about 1,000 square microns in diameter, about 125 square microns in diameter to about 250 square microns in diameter, about 125 square microns in diameter to about 500 square microns in diameter, about 125 square microns in diameter to about 750 square microns in diameter, about 125 square microns in diameter to about 1,000 square microns in diameter, about 250 square microns in diameter to about 500 square microns in diameter, about 250 square microns in diameter to about 750 square microns in diameter, about 250 square microns in diameter to about 1,000 square microns in diameter, about 500 square microns in diameter to about 750 square microns in diameter, about 500 square microns in diameter to about 1,000 square microns in diameter, or about 750 square microns in diameter to about 1,000 square microns in diameter. A circular agent transfer array element can be about 25 square microns in diameter, about 50 square microns in diameter, about 125 square microns in diameter, about 250 square microns in diameter, about 500 square microns in diameter, about 750 square microns in diameter, or about 1,000 square microns in diameter.

In some embodiments, more than one agent transfer array element is printed on an agent transfer device such that the agent transfer array elements form a grid. In some embodiments, the grid comprises about 10 agent transfer array elements to about 10,000 agent transfer array elements. In some embodiments, the grid comprises at least about 10 agent transfer array elements. In some embodiments, the grid comprises at most about 10,000 agent transfer array elements. In some embodiments, the grid comprises about 10 agent transfer array elements to about 100 agent transfer array elements, about 10 agent transfer array elements to about 1,000 agent transfer array elements, about 10 agent transfer array elements to about 10,000 agent transfer array elements, about 100 agent transfer array elements to about 1,000 agent transfer array elements, about 100 agent transfer array elements to about 10,000 agent transfer array elements, or about 1,000 agent transfer array elements to about 10,000 agent transfer array elements. In some embodiments, the grid comprises about 10 agent transfer array elements, about 100 agent transfer array elements, about 1,000 agent transfer array elements, or about 10,000 agent transfer array elements.

The agent transfer array elements may be designed to accommodate a wide range of volumes. In some embodiments, the maximum volume of the agent transfer array elements is about 2 picoliters to about 10,000 picoliters. In some embodiments, the maximum volume of the agent transfer array elements is at least about 2 picoliters. In some embodiments, the maximum volume of the agent transfer array elements is at most about 10,000 picoliters. In some embodiments, the maximum volume of the agent transfer array elements is about 2 picoliters to about 10 picoliters, about 2 picoliters to about 50 picoliters, about 2 picoliters to about 100 picoliters, about 2 picoliters to about 250 picoliters, about 2 picoliters to about 500 picoliters, about 2 picoliters to about 1,000 picoliters, about 2 picoliters to about 10,000 picoliters, about 10 picoliters to about 50 picoliters, about 10 picoliters to about 100 picoliters, about 10 picoliters to about 250 picoliters, about 10 picoliters to about 500 picoliters, about 10 picoliters to about 1,000 picoliters, about 10 picoliters to about 10,000 picoliters, about 50 picoliters to about 100 picoliters, about 50 picoliters to about 250 picoliters, about 50 picoliters to about 500 picoliters, about 50 picoliters to about 1,000 picoliters, about 50 picoliters to about 10,000 picoliters, about 100 picoliters to about 250 picoliters, about 100 picoliters to about 500 picoliters, about 100 picoliters to about 1,000 picoliters, about 100 picoliters to about 10,000 picoliters, about 250 picoliters to about 500 picoliters, about 250 picoliters to about 1,000 picoliters, about 250 picoliters to about 10,000 picoliters, about 500 picoliters to about 1,000 picoliters, about 500 picoliters to about 10,000 picoliters, or about 1,000 picoliters to about 10,000 picoliters. In some embodiments, the maximum volume of the agent transfer array elements is about 2 picoliters, about 10 picoliters, about 50 picoliters, about 100 picoliters, about 250 picoliters, about 500 picoliters, about 1,000 picoliters, or about 10,000 picoliters.

C. Detection Techniques

Biomolecules extracted from the at least one region of interest are then detected to analyze the biomolecule expression profile of cells within the region of interest, or the genomic DNA composition of cells within the region of interest (e.g. in the case of a tissue sample containing cancerous cells, wherein the genomic DNA of cells within the tissue section may be heterogeneous due to mutations, deletions, and/or translocations). Thus, the methods, devices, and compositions contained herein can be used to analyze both genetic and epigenetic features of cells within the region of interest.

In some methods, expression levels of biomolecules (e.g. mRNA, or cDNA derived from mRNA by reverse-transcription, or genomic DNA) within the at least one region of interest are determined by sequencing. Sequencing methods may include: Next Generation sequencing, high-throughput sequencing, pyrosequencing, classic Sanger sequencing methods, sequencing-by-ligation, sequencing by synthesis, sequencing-by-hybridization, RNA-Seq (Illumina), digital PCR, Digital Gene Expression (Helicos), next generation sequencing, single molecule sequencing by synthesis (SMSS) (Helicos), Ion Torrent Sequencing Machine (Life Technologies/Thermo-Fisher), massively-parallel sequencing, clonal single molecule Array (Solexa), shotgun sequencing, Maxim-Gilbert sequencing, and primer walking.

In some methods, expression levels of biomolecules (e.g. mRNA, or cDNA derived from mRNA by reverse-transcription) within the at least one region of interest are determined by so-called "real time amplification" methods also known as quantitative PCR (qPCR) or Taqman (see, e.g., U.S. Pat. No. 5,210,015 to Gelfand, U.S. Pat. No. 5,538,848 to Livak, et al., and 5,863,736 to Haaland, as well as Heid, C. A., et al., Genome Research, 6:986-994 (1996); Gibson, U. E. M, et al., Genome Research 6:995-1001 (1996); Holland, P. M., et al., Proc. Natl. Acad. Sci. USA 88:7276-7280, (1991); and Livak, K. J., et al., PCR Methods and Applications 357-362 (1995)). The basis for this method of monitoring the formation of amplification product is to measure continuously PCR product accumulation using a dual-labeled fluorogenic oligonucleotide probe. The probe used in such assays is typically a short (ca. 20-25 bases) polynucleotide that is labeled with two different fluorescent dyes. The 5' terminus of the probe is typically attached to a reporter dye and the 3' terminus is attached to a quenching dye The probe is designed to have at least substantial sequence complementarity with a site on the target mRNA or nucleic acid derived from. Upstream and downstream PCR primers that bind to flanking regions of the locus are also added to the reaction mixture. When the probe is intact, energy transfer between the two fluorophores occurs and the quencher quenches emission from the reporter. During the extension phase of PCR, the probe is cleaved by the 5' nuclease activity of a nucleic acid polymerase such as Taq polymerase, thereby releasing the reporter from the polynucleotide-quencher and resulting in an increase of reporter emission intensity which can be measured by an appropriate detector. The recorded values can then be used to calculate the increase in normalized reporter emission intensity on a continuous basis and ultimately quantify the amount of the mRNA being amplified.

In some embodiments, for qPCR or Taqman detection, an RT-PCR step is first performed to generate cDNA from cellular RNA. Such amplification by RT-PCR can either be general (e.g. amplification with partially/fully degenerate oligonucleotide primers) or targeted (e.g. amplification with oligonucleotide primers directed against specific genes which are to be analyzed at a later step).

In some embodiments, qPCR or Taqman are used immediately following a reverse-transcriptase reaction performed on isolated cellular mRNA; this variety serves to quantitate the levels of individual mRNAs during qPCR.

For qPCR or Taqman, the levels of particular genes may be expressed relative to one or more internal control gene measured from the same sample using the same detection methodology. Internal control genes may include so-called "housekeeping" genes (e.g. ACTB, B2M, UBC, GAPD and HPRT1).

In some embodiments, for qPCR or Taqman detection or RNA sequencing, a "pre-amplification" step is first performed on cDNA transcribed from cellular RNA. This serves to increase signal in conditions where the natural level of the RNA/cDNA to be detected is very low. Suitable methods for pre-amplification include but are not limited LM-PCR, PCR with random oligonucleotide primers (e.g. random hexamer PCR), PCR with poly-A specific primers, and any combination thereof. The pre-amplification may be either general or targeted in the same way as the reverse-transcription reaction described above.

mRNA levels can also be measured without amplification by hybridization to a probe, for example, using a branched nucleic acid probe, such as a QuantiGene® Reagent System from Panomics.

Alternatively or additionally, expression levels of genes from the at least one region of interest can be determined at the protein level, meaning that levels of proteins encoded by the genes discussed above are measured. Several methods and devices are well known for determining levels of proteins including immunoassays such as described in e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792. These assays include various sandwich, competitive, or non-competitive assay formats, to generate a signal that is related to the presence or amount of an protein analyte of interest. Any suitable immunoassay may be utilized, for example, lateral flow, enzyme-linked immunoassays (ELISA), radioimmunoassays (RIAs), competitive binding assays, and the like. Numerous formats for antibody arrays have been described proposed employing antibodies. Such arrays typically include different antibodies having specificity for different proteins intended to be detected. For example, usually at least one hundred different antibodies are used to detect one hundred different protein targets, each antibody being specific for one target. Other ligands having specificity for a particular protein target can also be used, such as the synthetic antibodies disclosed in WO/2008/048970. Other compounds with a desired binding specificity can be selected from random libraries of peptides or small molecules. U.S. Pat. No. 5,922,615 describes a device that utilizes multiple discrete zones of immobilized antibodies on membranes to detect multiple target antigens in an array. U.S. Pat. Nos. 5,458,852, 6,019,944, 6,143,576. Microtiter plates or automation can be used to facilitate detection of large numbers of different proteins. Protein levels can also be determined by mass spectrometry (e.g. tandem LC/MS/MS). In some embodiments, genomic DNA isolated from a region of interest is analyzed (e.g. by any of the sequencing techniques mentioned above, or by qPCR). Such analysis may serve to detect genomic variations including but not limited to variations in nucleotide sequence in and around genes, the presence of SNPs, insertions, deletions, and/or copy number variations. In some variations of this embodiment, isolated DNA is first amplified by a whole-genome amplification (WGA) technique to improve the ability to DNA sequences from limited samples.

In some embodiments, the WGA technique is a two-stage technique known as degenerate-oligonucleotide-primed (DOP) PCR. In the first stage, DOP-PCR uses primers containing a) a random six nucleotide sequence on their 3' end, and b) a fixed adapter sequence (optionally containing a barcode comprising a sample index and/or a unique molecular identifier) with an optimal Tm for PCR amplification; the random primers are hybridized to the sample at a low annealing temperature followed by strand extension using a polymerase at a higher temperature. In the second stage, primers containing a 3' end complementary to the 5' fixed adapter sequence of the first-stage primers (and optionally including a barcode comprising a sample index and/or a unique molecular identifier on their 5' end) are used to amplify the products from the first stage using PCR annealing at a higher temperature than the first stage.

In some embodiments, the WGA technique is a one-stage isothermal technique known as multiple-displacement-amplification (MDA). MDA can use primers similar to the first stage of DOP-PCR, e.g. primers containing a) a random six nucleotide sequence on their 3' end, and b) a fixed adapter sequence (optionally containing a barcode comprising a sample index and/or a unique molecular identifier). However, instead of conventional PCR DNA polymerase such as Taq, MDA uses a strand-displacing polymerase such as (p29 DNA polymerase. The isolated DNA is amplified using the primers and (p29 DNA polymerase without cycling under isothermal conditions.

In some embodiments, the WGA technique is a quasi-linear amplification technique known as Multiple Annealing and Looping-Based Amplification Cycles (MALBAC). In the first stage, MALBAC uses specially-designed primers having a common 27-nucleotide sequence (e.g. GTG AGT GAT GGT TGA GGT AGT GTG GAG) at the 5' end and 8 random nucleotides at the 3' end; semi-amplicons are produced using these primers by first annealing at a low temperature (e.g. 15-20° C.), followed by extension using a strand displacing polymerase (e.g. Bst DNA polymerase) at a higher temperature (e.g. 70-75° C.). After melting the primers off the template (e.g. at 95° C. or higher), repeated cycles (e.g. 10+ cycles) of low temperature (e.g. 15-20° C.), high temperature (e.g. 70-75° C.), denaturing temperature (e.g. 95° C. or higher) and hairpin formation (e.g. 58° C.) are used to further amplify the semi-amplicons to full amplicons. Because the full amplicons contain identical 5' 27-nucleotide sequences (e.g. GTG AGT GAT GGT TGA GGT AGT GTG GAG), the hairpin formation step removes them from further participating in later cycles of amplification once they are made. This ensures more linear amplification, as copies of copies of copies from the original DNA are not made.

In some embodiments, the WGA technique is a derivative of Pico-Plex™ (Takara Bio) and/or is described in U.S. Pat. No. 8,206,913. These techniques and derivatives attempt to correct some of the problems associated with fully-random primer amplification of the whole genome (e.g. under-representation of certain regions). In some embodiments, self-inert (e.g. non-self-priming) degenerate primers are used in a first step of this method, which can be an isothermal amplification step or an initial annealing step at ~15-20° C. followed by an extension step at ~75° C. (e.g. with a mesophilic DNA polymerase). In some embodiments, these primers involve a) a 5' fixed region, b) a 3' variable region, and are designed such that the primers do not cross-hybridize or self-hybridize. In some embodiments, the variable region further comprises a partially degenerate sequence (e.g. 10 nt long, which can be all Ys, Rs, Ks, or Ms, wherein Y=random C or T; R=random A or G; M=random A or C; K=random G or T) and a fully degenerate sequence (e.g. 2 nt long, Ns, random A/C/T/G). In some embodiments the constant and variable regions of the self-inert degenerate primers consisting essentially of only two types of non-complementary nucleotides selected from the group consisting of adenines and guanines; adenines and cytosines; guanines and thymidines. In some embodiments, the self-inert degenerate primers used in the isothermal amplification step are according to any of SEQ ID NO 1-8 in Table 1 below.

TABLE 1 exemplary primer sequences

| SEQ ID NO: | SEQUENCE (Random bases definitions: K = G, T; N = A, G, C, T) |
|---|---|
| 1 | CCTTTCTCTCCCTTCTCTYYYYYYYYYYNN |
| 2 | AGAGAAGGGAGAGAAAGGRRRRRRRRRRNN |
| 3 | CCAAACACACCCAACACAMMMMMMMMMMNN |
| 4 | TGTGTTGGGTGTGTTTGGKKKKKKKKKKNN |
| 5 | CCTTTCTCTCCCTTCTCTYYYYYYYYYY |
| 6 | AGAGAAGGGAGAGAAAGGRRRRRRRRRR |
| 7 | CCAAACACACCCAACACAMMMMMMMMMM |
| 8 | TGTGTTGGGTGTGTTTGGKKKKKKKKKK |
| 9 | CCTTTCTCTCCCTTCTCT |
| 10 | AGAGAAGGGAGAGAAAGG |
| 11 | CCAAACACACCCAACACA |
| 12 | TGTGTTGGGTGTGTTTGG |

In some embodiments, an additional amplification step with a thermostable DNA polymerase is performed on the DNA amplified above. The additional amplification step can be performed using primers consisting of just the 5' fixed region from the primers used in the isothermal amplification step. In some embodiments, these primers are any of SEQ ID NO 8-12 in Table 1. The additional amplification step can comprise >10 cycles of normal PCR cycling (e.g. denaturing, annealing, extension) using the thermostable DNA polymerase. In some embodiments, the cycling conditions incorporate an additional lower temperature step after the extension step to promote the formation of hairpin DNA similar to the method of MALBAC above.

EXAMPLES

Example 1A. —Protocol for Application of Hydrophobic Mask to Tissue Sections

A computer-assisted inkjet system is used to apply a grid pattern of coating to a tissue sample such that a plurality of regularly-spaced non-coated regions are created. The coating comprises a non-fluorinated acrylate or cyanoacrylate mixed with a fluoroalkyl acrylate monomer as described herein in an alcohol or ketone solvent plus photoinitiator. The section is then exposed briefly to UV light to cure the coating.

Example 1B. —Alternate Protocol for Application of Hydrophobic Mask to Tissue Sections A computer-assisted inkjet system is used to apply a grid pattern of a first coating to a tissue sample such that a plurality of regularly-spaced non-coated regions are created. The first coating comprises a non-fluorinated acrylate or cyanoacrylate plus photoinitiator. The first coating is briefly exposed to UV light to cure. Next, also using a computer-assisted inkjet system, a second coating comprising a fluoroalkyl acrylate monomer as described herein plus photoinitiator is added over the first coating. The second coating is then cured by brief exposure to UV light.

Example 2.—Isolation of Regions of Interest in a Tissue Sample Using Hydrophobic Chemistry FFPE hepatocellular carcinoma tissue sections were subjected to hematoxylin/eosin staining with or without deparaffinization and with or without hydrophobic masking of regions of interest using a fluoroalkyl acrylate monomer. A picture of the resultant slides is presented in FIG. 1. Deparaffinization of an FFPE tissue section followed by treatment with the hydrophobic chemistry of Example 1 caused effective aqueous isolation of the masked regions of interest, preventing their staining with hematoxylin/eosin.

Figure 2A:
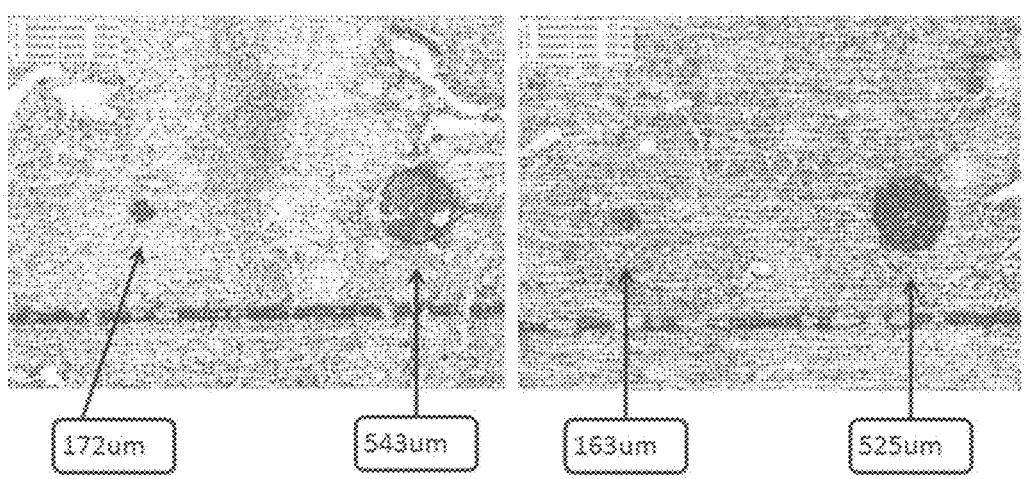
Figure 2B:
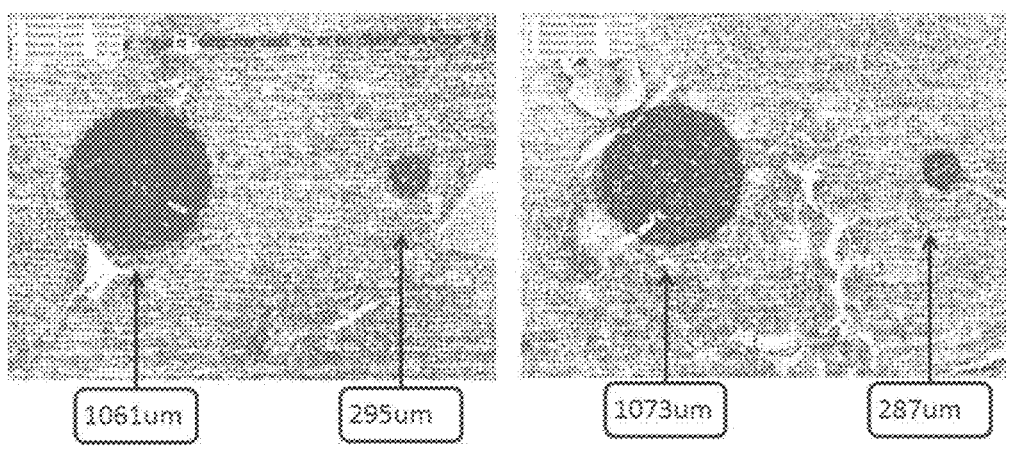
Figure 2C:
Figure 2D:
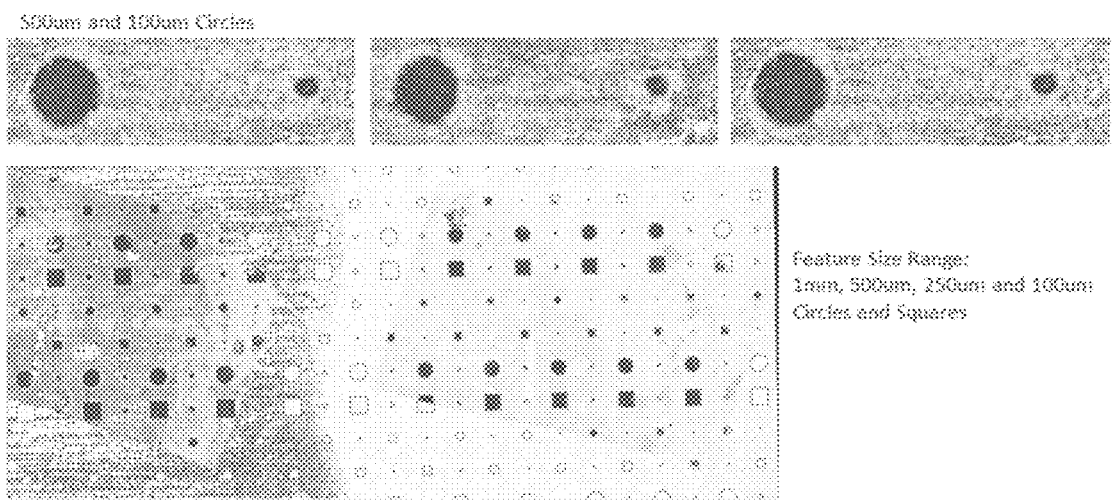
Figure 2F:
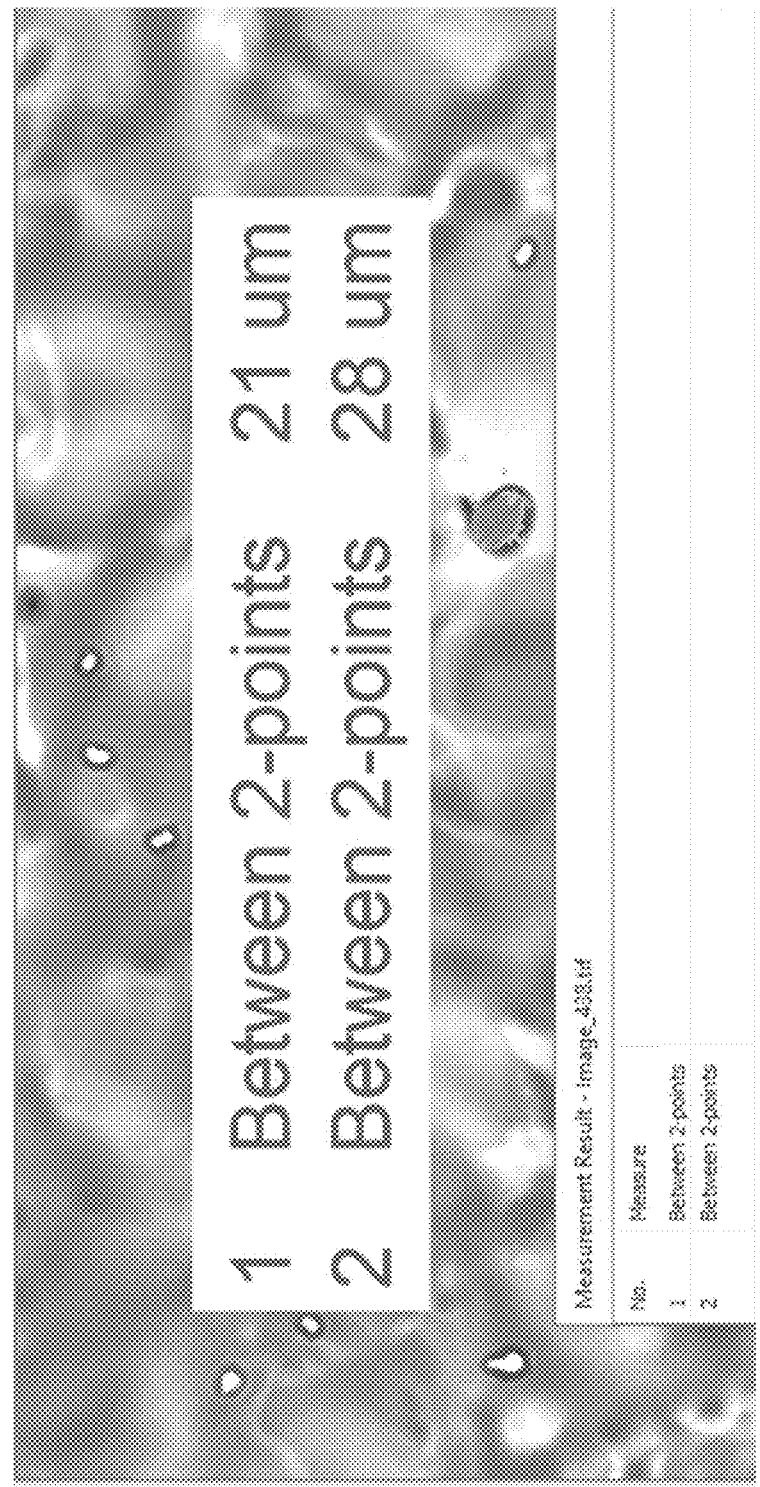

Example 3.—Isolation of Regions of Varying Size in FFPE Mouse Liver Sections FFPE mouse liver sections were deparaffinized and masked to isolate regions of varying size (100, 250, 500, 1000 microns in diameter) and shape (square and circle), and stained with hematoxylin/eosin to demonstrate the hydrophilic accessibility of the regions of interest (and inaccessibility of the surrounding hydrophobic mask), as well as the accuracy/precision of ink-jet application of the mask. FIG. 2A shows that regions of ~160 or ~550 microns in diameter can be clearly defined using ink-jet printing of the chemical mask. FIG. 2B shows that regions of ~300 or ~1000 microns in diameter can be clearly defined using ink-jet printing of the chemical mask. FIG. 2C demonstrates that both circular and polygonal shapes can be isolated from sections. FIG. 2E shows that regions of diameter 2 mm can be clearly defined on sections. FIG. 2D shows that regions of varying diameter (100, 250, 500, 1 mm) and shape (square and circle) can be printed in a clearly defined grid on a single tissue section.

Example 4.—Hydrophobic Masking Blocks Extraction of Nucleic Acids from Masked Regions FFPE tissue sections were masked according to the method of Example 1A or Example 1B to generate regions of interest having varying sizes.

Slides were deparaffinized by baking in a 55-60° C. oven for 1 hour, dipping twice in xylene for 3 minutes, dipping twice in 100% ethanol for 3 minutes. Slides were optionally stored in ethanol for up to one month.

For further analysis, slides were air-dried to remove the ethanol and the tissue was lysed. Adhesive chambers were attached to the slide circumscribing the tissue region, 600 microliters of proteinase-K containing Qiagen tissue lysis buffer ATL were added, the chamber was sealed with adhesive film, and the slide was incubated on a heat block at 56° C. for one hour. The liquid (~450 microliters) was collected from the slide chambers in microfuge tubes, and then the microfuge tubes were heated at 90° C. for 1 hour. The microfuge tubes were then centrifuged to pellet the insoluble material, and the supernatant was removed to a new tube and treated with 45 microliters of RNAse A (100 mg/ml) followed by incubation at room temperature for 2 minutes. An equal volume of Qiagen buffer AL (~500 microliters) was added to the supernatant, and the sample was mixed by vortexing. Following vortexing, an equal amount of 100% ethanol (~500 microliters) was added to the supernatant and the entire solution was transferred to a Qiagen min-elute column. The columns were washed using buffer AW1 and AW2 according to manufacturer's instructions, and nucleic acids were eluted in Qiagen buffer ATE. Nucleic acids from each sample were then quantified on a Qubit spectrophotometer. The relationship between size of region of interest and DNA extracted is presented in Table 2. The data on DNA yield vs uncoated surface area indicates the DNA yield is proportional to the area covered, suggesting that DNA is not extracted areas of the tissue section covered by the hydrophobic coating.

TABLE 2

Uncoated surface area vs DNA yield for hydrophobic coated slide

| Sample | Description | Area (mm2) of nucleic acid extractions | DNA yield ng/microliters |
|---|---|---|---|
| 1 | Slide with no coating | 220 | 1.24 |
| 2 | 2 mm features, circles @ 2.5 mm pitch | 110 | 0.456 |
| 3 | 1 mm features, circles @ 2 mm pitch | 44 | 0.316 |
| 4 | Slide completely covered with coating | 0 | 0.193 |

Example 5.—Optimized Hydrophobic Coating Procedure

A) Procedure for Small Features (<1 mm Diameter)

If the tissue sample is an FFPE sample, the tissue sample is first subjected to deparaffinization by standard procedures (e.g. baking in an oven at approximately 60 degrees for 1 hour, followed by incubations in xylene for 3 min, xylene for 3 min, 100% EtOH for 3 min, 100% EtOH for 3 min, and air drying for 5 min). The tissue surface is coated with an initial hydrophobic coating by spray or dipping in an alcohol solution containing a fluoroacrylate with or micron-sized fluoroparticulates; examples include but are not limited to Fluoro-pel 800 or 800M. The slide is then air-dried (this initial treatment improves definition of small features by the following cyanoacrylate printing step).

A solution of cyanoacrylate containing a photoinitiator is ink-jet printed on the tissue sample to form a mask over the areas desired to be excluded, or the areas separating the desired features. During the printing, the cyanoacrylate is pinned via exposure to UV light (e.g. 395 nm @~ 400 mJ/cm2) for a minimum of a second after deposition. The slide is then removed from the printing apparatus and immediately subjected to an extended UV cure (e.g. 395 nm at ~400 mJ/cm2 for about 5 mins).

Following UV cure, the entire slide is subjected to vacuum-assisted vapor-phase deposition of a perfluoroalkyltrichlorosilane (e.g. FOTS, Trichloro(1H,1H,2H,2H-perfluorooctyl)silane)). Application of this technique has allowed generations of circular regions of interest on FFPE human liver tissue sections with diameters as small as 25 microns.

B) Procedure for Large Features (Approximately about 1 mm or Greater)

If the tissue sample is an FFPE sample, the tissue sample is first subjected to deparaffinization by standard procedures (e.g. baking in an oven at approximately 60 degrees for 1 hour, followed by incubations in xylene for 3 min, xylene for 3 min, 100% EtOH for 3 min, 100% EtOH for 3 min, and air drying for 5 min). Larger features can forego the initial fluoroalkyl coating. A solution of cyanoacrylate containing a photoinitiator is ink-jet printed on the tissue sample in the areas desired to be excluded, or the areas separating the desired features. During the printing, the cyanoacrylate is pinned via exposure to UV light (e.g. 395 nm @ ~ 400 mJ/cm2) for a minimum of a second after deposition. The slide is then removed from the printing apparatus and immediately subjected to an extended UV cure (e.g. 395 nm at ~400 mJ/cm2 for about 5 mins).

Following UV cure, the entire slide is subjected to vacuum-assisted vapor-phase deposition of a perfluoroalkyl silane (e.g. Trichloro(1H,1H,2H,2H-perfluorooctyl)silane).

Example 6.—Lysis and Isolation of Hydrophobicity-Separated Regions

A surface tension array is prepared as in US20150268233 A1 or Butler et al. J. Am. Chem. Soc. 2001, 123, 8887-8894 with hydrophilic features corresponding to the nonexcluded areas of the mask applied to the tissue sample above. This derivatization procedure involves coating a quantitatively clean glass slide with a monofunctional (one attachment site for silanation) organosilane such as 3-aminopropyldimethylethoxysilane (APDMS) followed by protection of the non-excluded areas/hydrophilic regions with positive photoresist and treatment with an anti-stiction coating such as a per-fluoroalkylsilane (e.g. tridecafluoro-1,1,2,2-tetrahydrooctyl) trichlorosilane.

A suitable lysis buffer containing detergent is applied to the hydrophilic features of the surface tension array. The surface tension array containing the hydrophilic regions bearing lysis buffer is contacted to the tissue sample prepared as in Examples 1A, 1B, or 5. The contact is allowed for a suitable period of time to allow for cell lysis. The surface tension array (which now contains lysis buffer comprising lysed cellular components) is removed from contact with the tissue section, and the individual spots on the surface tension array are interrogated for a desired property (e.g. protein or nucleic acid abundance, sequence, or both).

Example 7.—Contact Angle Measurements on Coated Surfaces

FFPE tissue sections or glass slides were subjected to different stages of the coating procedure presented in example 5B were subjected with different lengths of vapor phase coating with FOTS ((tridecafluoro-1,1,2,2-tetrahydrooctyl) trichlorosilane). Contact angle measurements were performed using direct measurement by Telescope-Goniometer (see e.g. Bracco and Holst. Surface Science Techniques. 2013. ISBN 978-3-642-34243-1. pp. 3-34.) The data demonstrate that addition of cyanoacrylate on top of the tissue section enhances coating by FOTS, and that the combination of the two increase the contact angle of the combined FOTS/cyanoacrylate tissue surface to the very hydrophobic (greater than 110 contact angle) range.

TABLE 3

Contact angle measurements for tissue or glass with various coatings

| Surface (after treatment with FOTS) | FOTS Time incubated (hr) | Pre-incubation angle | Post-incubation angle | Angle change | Notes |
|---|---|---|---|---|---|
| Tissue | 4 | 130 | 109 | −21 | Suggests that the FS is not covalently bound. |
| Glass | 4 | 90 | 108.4 | 18.4 | Strongly suggests that the FS is covalently bound. |
| Cyanoacrylate on tissue | 4 | 91.4 | 112 | 20.6 | Strongly suggests that the FS is covalently bound. |
| Cyanoacrylate on glass | 4 | 100.5 | 105.3 | 4.8 | Strongly suggests that the FS is covalently bound. |
| Tissue | 2 | 130 | 92.7 | −37.3 | Suggests that the FS is not covalently bound. |
| Glass | 2 | 90 | 120 | 30 | Strongly suggests that the FS is covalently bound. |
| Cyanoacrylate on tissue | 2 | 95 | 111 | 16 | Strongly suggests that the FS is covalently bound. |
| Cyanoacrylate on glass | 2 | 90 | 105.7 | 15.7 | Strongly suggests that the FS is covalently bound. |
| Tissue | 1 | 120 | 88.5 | −31.5 | Suggests that the FS is not covalently bound. |
| Glass | 1 | 88 | 114 | 26 | Strongly suggests that the FS is covalently bound. |
| Cyanoacrylate on tissue | 1 | 100.7 | 102.7 | 2 | Strongly suggests that the FS is covalently bound. |
| Cyanoacrylate on glass | 1 | 86 | 90 | 4 | Strongly suggests that the FS is covalently bound. |

Example 8.—qPCR of RNA Isolated from Hydrophobic Masked FFPE Tissue Sections

Various serial sections from the same FFPE breast cancer tissue sample (Biomax™, huCAT299) were subjected to the optimized coating procedure of Example 5 to select various different regions of interest comprising non-cancerous tissue, transitional tissue (e.g. some non-cancerous and some cancerous tissue), and cancerous tissue (see FIGS. 7 and 8, wherein the left side of FIG. 8 demonstrates the different mask patterns applied to the various tissue layers/sections, and the right side demonstrates the various tissue regions of interest isolated post-masking). Following coating, the regions of interest were lysed by application of a detergent-containing lysis buffer plus proteinase K to the slide (lysis buffer was also applied to coated regions as a control). Total RNA was extracted from the samples shown in FIG. 8 by placing the lysis buffer directly on to the regions and incubating for 1 hr at 56 C. Total RNA was purified following the manufacturer's protocol using the NucleoSpin™ totalRNA FFPE XS kit (Takara Bio), and RNA amounts from the samples were quantified by Qubit fluorescence assay. A panel of qPCR assays was performed on the RNA extracted from the samples to detect genes known to be enriched in breast cancer (see FIG. 9, which depicts qPCR Ct values of individual known tumor-enriched genes from the sample). The analysis indicated that in the tumor sample, as expected, levels of the genes detected by qPCR was more characteristic of cancerous tissue than healthy tissue, indicating that the mask is effective to isolate tissue regions for selective lysis, and that the hydrophobic coating procedure does not interfere with downstream amplification of nucleic acids liberated from defined regions of interest.

The RNA samples isolated by the masking procedure described above were also compared to a conventional manual spatial isolation technique performed on the same samples (labeled "tube" in FIG. 9 panel B). qPCR Ct counts were calculated relative to the housekeeping gene GAPDH, and the data were graphed (FIG. 9). Expression levels of the genes via both methods were found to be highly correlated, indicating that the hydrophobic masking procedure is equivalent to the manual isolation workflow.

Additionally, for an exemplary masked tissue region, the amount of nucleic acid liberated by lysis buffer applied to masked or unmasked regions was compared (FIG. 9 panel C). The analysis demonstrates that dramatically less nucleic acid was isolated from covered regions, indicating that the hydrophobic mask is effective to exclude non-desired tissue from lysis in the procedure.

Additionally, a set of 177 qPCR assays designed to detect genes selectively expressed in breast cancer were performed on the RNA isolated from the masked tumor sample. 177 unique expressed qPCR products were detected within the RNA liberated from the cancerous sample by the masking procedure, indicating that a wide portion of the expressed genome has been isolated from the cancerous cells isolated by the masking procedure.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

---

What is claimed is:

1. A method of isolating cellular components from at least one region of interest within a planar tissue section disposed onto a solid substrate, comprising:
   (a) circumscribing at least one region of interest within the planar tissue section disposed onto the solid substrate by applying a chemical mask to the planar tissue section;
   (b) solubilizing the cellular components within the at least one region of interest by dispensing a first solution comprising one or more extraction agents into the at least one region of interest whereby cells circumscribed within the at least one region of interest are selectively lysed, and a convex liquid dome is formed within each region of the at least one region of interest wherein the convex liquid dome is isolated from a fluid communication with other convex liquid domes in other regions of interest of the at least one region of interest and the other convex liquid domes are isolated from a fluid communication with each other.

2. The method of claim 1, wherein the dispensing the first solution onto the region of interest comprises:
   (a) dispensing the first solution into an agent transfer device comprising at least one agent transfer array element positioned on a surface of a second solid substrate;
   (b) contacting the at least one agent transfer array element positioned on the surface of the second solid substrate with the planar tissue section, such that the at least one agent transfer array element spatially corresponds to the at least one region of interest in the planar tissue section, wherein the contacting enables a transfer of the first solution to the at least one region of interest in the planar tissue section.

3. The method of claim 1, further comprising isolating at least one solubilized cellular component from the at least one region of interest within the planar tissue section on the solid substrate.

4. The method of claim 1, further comprising sequencing nucleic acids among the at least one cellular component solubilized from the at least one region of interest.

5. The method of claim 1, further comprising analyzing proteins among the at least one cellular component solubilized from the at least one region of interest using a tandem mass spectrometer.

6. The method of claim 1, wherein the dispensing the first solution is performed with the first solution further comprising a soluble tag, wherein the soluble tag corresponds to the at least one region of interest.

7. The method of claim 6, wherein the dispensing the first solution is performed with the first solution comprising the soluble tag being an oligonucleotide.

8. The method of claim 7, wherein the dispensing the first solution is performed with the first solution comprising the oligonucleotide further comprising a sample index sequence corresponding to the region of interest and, optionally, a unique molecular identifier sequence.

9. The method of claim 7, wherein the dispensing the first solution is performed with the first solution comprising the oligonucleotide comprising a charge tag corresponding to the region of interest.

10. The method of claim 7, wherein the dispensing the first solution is performed with the first solution comprising the oligonucleotide being double-stranded.

11. The method of claim 7, wherein the dispensing the first solution is performed with the first solution comprising the oligonucleotide being conjugated to a bead.

12. The method of claim 6, wherein the dispensing the first solution is performed with the first solution comprising the soluble tag being a Tandem Mass Tag.

13. The method of claim 1, wherein the dispensing the first solution is performed with the one or more extraction agents comprising surfactants, proteases, tonicity adjusting agents, chaotropes, nucleases, buffers, protease inhibitors, phosphatase inhibitors, or nuclease inhibitors or a combination thereof.

14. The method of claim 1, wherein the applying the chemical mask is performed with the chemical mask having a contact angle between 60 degrees and 155 degrees.

15. The method of claim 1, wherein the applying the chemical mask is performed using a hydrophobic mask solution comprising a fluoropolymer or a fluoroacrylic polymer.

16. The method of claim 15, wherein the applying the chemical mask is performed using a second comprising an acrylate solution or cyano-acrylate solution.

17. The method of claim 16, wherein the applying the chemical mask is performed with the chemical mask solution further comprising a solvent.

18. The method of claim 17, wherein the applying the chemical mask is performed with chemical mask solution comprising the solvent being a propylene glycol derivative solvent, a fluorocarbon solvent, or an alcohol solvent.

19. The method of claim 17, wherein the applying the chemical mask is performed with chemical mask solution comprising the solvent being a perfluorooctane solvent, a perfluoro-2-methylpentane solvent, a perfluoro-1,3-dimethylcyclohexane solvent, a perfluorodecalin solvent, or a 1,3-difluoropropane solvent.

20. The method of claim 1, wherein each region of interest of the at least one region of interest is less than about $7.8 \times 10^5$ square microns in area.

21. The method of claim 2, wherein the dispensing the first solution is performed with the at least one agent transfer array element positioned on the surface of the second solid substrate comprising at least one hydrophilic region circumscribed by a hydrophobic region.

22. The method of claim 1, further comprising solubilizing cellular components from more than one region of interest in the planar tissue.

23. The method of claim 1, wherein the applying the chemical mask is performed with the chemical mask circumscribing the at least one region of interest in the planar tissue section on the solid substrate being applied to the planar tissue section using a piezoelectric ink-jet delivery device.

24. The method of claim 1, wherein the applying the chemical mask is performed with the planar tissue section being about 2 to about 50 μm in thickness.

25. The method of claim 1, wherein the applying the chemical mask is performed with the planar tissue section being about 1 to about 15 μm in thickness.

26. The method of claim 1, wherein the applying the chemical mask is performed with the planar tissue section being a formalin fixed, paraffin embedded (FFPE) tissue section.

27. The method of claim 1, wherein the applying the chemical mask is performed with the planar tissue section being an unfixed tissue section.

28. The method of claim 1, further comprising dispensing a second solution comprising one or more extraction agents onto the region of interest whereby a droplet containing liberated cellular components is formed, wherein the droplet is isolated from a fluid communication with a tissue outside the region of interest without the isolated droplet isolation being mediated by a solid physical barrier between the liberated cellular components and the tissue outside the region of interest.

* * * * *